United States Patent
Kato et al.

(10) Patent No.: US 9,957,213 B2
(45) Date of Patent: May 1, 2018

(54) ORGANIC COMPOUND, LIQUID CRYSTAL COMPOSITION, LIQUID CRYSTAL ELEMENT, AND LIQUID CRYSTAL DISPLAY DEVICE

(71) Applicant: SEMICONDUCTOR ENERGY LABORATORY CO., LTD., Atsugi-shi, Kanagawa-ken (JP)

(72) Inventors: Momoko Kato, Fukushima (JP); Yasuhiro Niikura, Kanagawa (JP); Makoto Ikenaga, Kanagawa (JP); Manabu Kobayashi, Tokyo (JP); Tetsuji Ishitani, Kanagawa (JP)

(73) Assignee: SEMICONDUCTOR ENERGY LABORATORY CO., Kanagawa-ken (JP)

( * ) Notice: Subject to any disclaimer, the term of this patent is extended or adjusted under 35 U.S.C. 154(b) by 0 days. days.

(21) Appl. No.: 14/330,012

(22) Filed: Jul. 14, 2014

(65) Prior Publication Data
US 2015/0034870 A1 Feb. 5, 2015

(30) Foreign Application Priority Data
Jul. 30, 2013 (JP) ................... 2013-157919

(51) Int. Cl.
*G02F 1/1333* (2006.01)
*C07C 43/21* (2006.01)
*C07C 43/205* (2006.01)
*C09K 19/20* (2006.01)
*C09K 19/30* (2006.01)
*C09K 19/58* (2006.01)

(52) U.S. Cl.
CPC ............ *C07C 43/21* (2013.01); *C07C 43/205* (2013.01); *C09K 19/20* (2013.01); *C09K 19/3066* (2013.01); *C09K 19/586* (2013.01); *C07C 2101/14* (2013.01)

(58) Field of Classification Search
CPC .. C09K 19/20; C09K 19/3066; C09K 19/586; C07C 43/21; C07C 43/205; C07C 2101/14; G03F 1/1333
USPC ....................... 252/299.6; 349/182
See application file for complete search history.

(56) References Cited

U.S. PATENT DOCUMENTS

| | | | | |
|---|---|---|---|---|
| 5,217,645 | A | * | 6/1993 | Iwaki ................... C09K 19/406 252/299.01 |
| 5,849,217 | A | * | 12/1998 | Nakamura ........... C07D 307/33 219/445.1 |
| 7,576,829 | B2 | | 8/2009 | Kikuchi et al. |
| 8,440,102 | B2 | | 5/2013 | Tamura et al. |
| 8,603,595 | B2 | | 12/2013 | Kawakami et al. |
| 8,668,964 | B2 | | 3/2014 | Kato et al. |
| 8,758,870 | B2 | | 6/2014 | Niikura et al. |
| 2008/0259254 | A1 | | 10/2008 | Kikuchi et al. |
| 2011/0090183 | A1 | | 4/2011 | Yamazaki et al. |
| 2013/0134352 | A1 | | 5/2013 | Kato et al. |
| 2013/0155368 | A1 | | 6/2013 | Niikura et al. |
| 2013/0256594 | A1 | | 10/2013 | Kato et al. |
| 2013/0256595 | A1 | | 10/2013 | Ikenaga et al. |
| 2013/0321745 | A1 | | 12/2013 | Kubota |

FOREIGN PATENT DOCUMENTS

| | | | | |
|---|---|---|---|---|
| JP | 7-101951 | * | 4/1995 | ............. C09K 19/54 |
| JP | 2010-175940 | A * | 8/2010 | ........... G02F 1/1343 |
| JP | 2011-141522 | | 7/2011 | |
| WO | WO-2009/109999 | | 9/2009 | |
| WO | WO 2011-046010 | | 4/2011 | |

* cited by examiner

*Primary Examiner* — Geraldina Visconti
(74) *Attorney, Agent, or Firm* — Nixon Peabody LLP; Jeffrey L. Costellia

(57) ABSTRACT

A novel organic compound that can be used in a variety of liquid crystal devices or a liquid crystal composition containing the novel organic compound is provided. An organic compound represented by General Formula (G1) is provided. A novel liquid crystal composition containing the organic compound is provided. In General Formula (G1), $Ar^1$ and $Ar^2$ separately represent a substituted or unsubstituted arylene group having 6 to 12 carbon atoms, a substituted or unsubstituted cycloalkylene group having 3 to 12 carbon atoms, or a substituted or unsubstituted cycloalkenylene group having 3 to 12 carbon atoms. In addition, m and n separately represent 0 or 1. $R^1$ and $R^2$ separately represent a hydrogen atom, a substituted or unsubstituted alkyl group having 1 to 11 carbon atoms, or a substituted or unsubstituted alkoxy group having 1 to 11 carbon atoms.

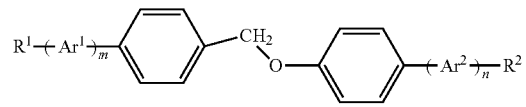

(G1)

9 Claims, 13 Drawing Sheets

ORGANIC COMPOUND, LIQUID CRYSTAL COMPOSITION, LIQUID CRYSTAL ELEMENT, AND LIQUID CRYSTAL DISPLAY DEVICE

BACKGROUND OF THE INVENTION

1. Field of the Invention

The present invention relates to an object, a method, or a manufacturing method. In addition, the present invention relates to a process, a machine, manufacture, or a composition of matter. In addition, one embodiment of the present invention relates to a semiconductor device, a display device, a driving method thereof, or a manufacturing method thereof. In particular, one embodiment of the present invention relates to a novel organic compound, a liquid crystal composition containing the novel organic compound, a liquid crystal element, a liquid crystal display device, and manufacturing methods thereof.

2. Description of the Related Art

In recent years, liquid crystals have been used in a variety of devices; in particular, liquid crystal display devices (liquid crystal displays) having advantages of thinness and lightness have been used for displays in a wide range of fields.

Low power consumption is an added value required of a liquid crystal display device. For example, in an active matrix liquid crystal display device, a transistor with low off-state current is used as a transistor having a function of applying voltage to a liquid crystal element; thus, data is rewritten at longer time intervals (a refresh rate is reduced) in a period during which one image (still image) is displayed, and power consumption is reduced (Patent Document 1).

REFERENCE

Patent Document

[Patent Document 1] Japanese Published Patent Application No. 2011-141522

SUMMARY OF THE INVENTION

To reduce power consumption of a liquid crystal display device, leakage of electrical charges accumulated between electrodes of a liquid crystal element needs to be as little as possible. This is because the leakage of electrical charges causes a change in voltage applied to a liquid crystal layer, resulting in a change in the transmittance of a pixel.

Particularly in driving of the liquid crystal display device at a low refresh rate, change in a still image over time needs to be prevented from being recognized by a user. However, when a change in voltage applied to the liquid crystal layer is bigger than that allowed as a deviation in a gray scale for displaying one image, a user perceives a flicker of the image, which means a decrease in display quality.

To reduce the leakage of electrical charges, an element with a high voltage holding ratio (VHR) is preferably used as the liquid crystal element in the liquid crystal display device. In addition, the use of the liquid crystal element with a high voltage holding ratio enables the liquid crystal display device to have high contrast.

A factor that influences the voltage holding ratio of a liquid crystal element is a decrease in the number of electrical charges due to a capacitance (C)-resistance (R) time constant of a liquid crystal layer. For this reason, the use of a material with high resistivity as a liquid crystal composition included in the liquid crystal layer can increase the voltage holding ratio of a liquid crystal element including the liquid crystal composition.

In view of the above, an object of one embodiment of the present invention is to provide a novel organic compound that can be used in a variety of liquid crystal devices.

Another object of one embodiment of the present invention is to provide a liquid crystal composition containing the novel organic compound and a liquid crystal element or a liquid crystal display device formed using the liquid crystal composition.

Another object of one embodiment of the present invention is to provide a liquid crystal composition with high resistivity. Another object of one embodiment of the present invention is to provide a liquid crystal element with a high voltage holding ratio.

Another object of one embodiment of the present invention is to provide a liquid crystal display device which consumes less power.

Note that the descriptions of these objects do not disturb the existence of other objects. In one embodiment of the present invention, there is no need to achieve all the objects. Objects other than the above objects will be apparent from and can be derived from the description of the specification and the like.

One embodiment of the present invention is an organic compound represented by General Formula (G1) below.

[Chemical Formula 1]

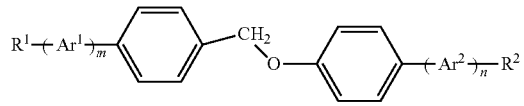

(G1)

In General Formula (G1), $Ar^1$ and $Ar^2$ separately represent a substituted or unsubstituted arylene group having 6 to 12 carbon atoms, a substituted or unsubstituted cycloalkylene group having 3 to 12 carbon atoms, or a substituted or unsubstituted cycloalkenylene group having 3 to 12 carbon atoms. In addition, m and n separately represent 0 or 1. $R^1$ and $R^2$ separately represent a hydrogen atom, a substituted or unsubstituted alkyl group having 1 to 11 carbon atoms, or a substituted or unsubstituted alkoxy group having 1 to 11 carbon atoms.

Another embodiment of the present invention is a liquid crystal composition containing the organic compound represented by General Formula (G1).

Other embodiments of the present invention are a liquid crystal element including the liquid crystal composition and a liquid crystal display device using the liquid crystal element.

One embodiment of the present invention makes it possible to provide a novel organic compound that can be used in a liquid crystal device.

One embodiment of the present invention makes it possible to provide a liquid crystal composition containing a novel organic compound, and a liquid crystal element and a liquid crystal display device each formed using the liquid crystal composition.

One embodiment of the present invention makes it possible to provide a liquid crystal composition which has high resistivity. One embodiment of the present invention makes it possible to provide a liquid crystal element which has a high voltage holding ratio.

One embodiment of the present invention makes it possible to provide a liquid crystal display device which consumes less power.

DETAILED DESCRIPTION OF THE INVENTION

Figure 1A:
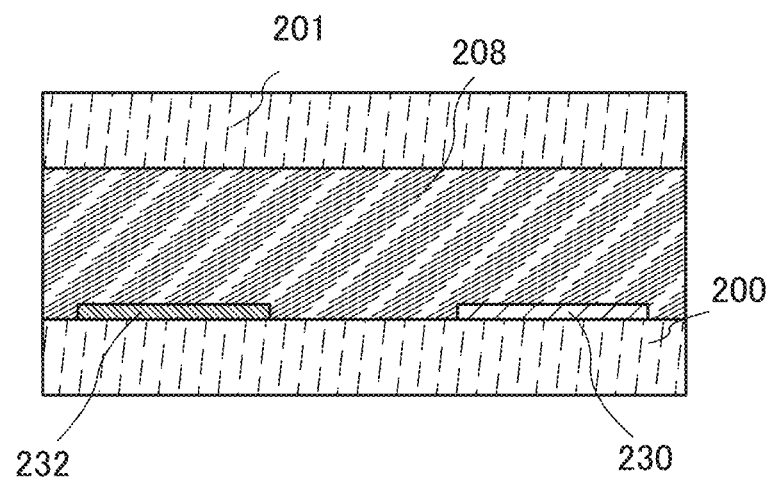
FIGS. 1A and 1B each illustrate one mode of a liquid crystal element and one mode of a liquid crystal display device.

Embodiments and examples of the invention disclosed in this specification will be described below with reference to the accompanying drawings. Note that the invention disclosed in this specification is not limited to the following description, and it is easily understood by those skilled in the art that modes and details of the invention can be modified in various ways. Therefore, the invention disclosed in this specification is not construed as being limited to the description of the following embodiments and examples. In the structures to be given below, the same portions or portions having similar functions are denoted by the same reference numerals in different drawings, and explanation thereof will not be repeated.

In addition, a liquid crystal display device in this specification and the like refers to an image display device or a light source (including a lighting device). A liquid crystal display device also refers to all the following modules: a module to which a connector, for example, a flexible printed circuit (FPC) or a tape carrier package (TCP) is attached, a module in which a printed wiring board is provided at the end of a TCP, and a module in which an integrated circuit (IC) is directly mounted on a display element by a chip on glass (COG) method. Note that a liquid crystal display device in this specification and the like refers to any type of electronic devices which utilizes liquid crystal characteristics; for example, a liquid crystal electro-optical device without display function is included in its category.

Note that ordinal numbers such as "first" and "second" in the following description are used for convenience and do not denote the order of steps or the stacking order of layers. Therefore, for example, description can be made even when "first" is replaced with "second", "third", or the like as appropriate. In addition, the ordinal numbers in this specification and the like are not necessarily the same as the ordinal numbers used to specify one embodiment of the present invention.

Embodiment 1

In this embodiment, a novel organic compound of one embodiment of the present invention will be described.

The novel organic compound of one embodiment of the present invention is represented by General Formula (G1) below.

[Chemical Formula 2]

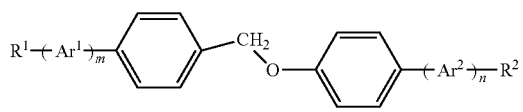

(G1)

In General Formula (G1), $Ar^1$ and $Ar^2$ separately represent a substituted or unsubstituted arylene group having 6 to 12 carbon atoms, a substituted or unsubstituted cycloalkylene group having 3 to 12 carbon atoms, or a substituted or unsubstituted cycloalkenylene group having 3 to 12 carbon atoms. In addition, m and n separately represent 0 or 1. $R^1$ and $R^2$ separately represent a hydrogen atom, a substituted or unsubstituted alkyl group having 1 to 11 carbon atoms, or a substituted or unsubstituted alkoxy group having 1 to 11 carbon atoms.

In General Formula (G1), examples of a substituent that can be bonded to $Ar^1$, $Ar^2$, $R^1$, or $R^2$ are electron-withdrawing substituents such as fluorine (F), bromine (Br), chlorine (Cl), iodine (I), a cyano group (CN), a trifluoromethyl group ($CF_3$), a trifluoromethylsulfonyl group ($SO_2CF_3$), a nitro group ($NO_2$), an isothiocyanate group (NCS), a thiocyanate group (SCN), and a pentafluorosulfanyl group ($SF_5$).

Structures represented by Structural Formulae (100) to (110) can be given as specific examples of the organic compound represented by General Formula (G1). However, the present invention is not limited thereto.

[Chemical Formulae 3]

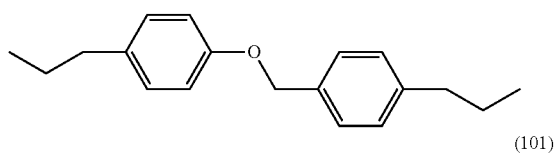

(100)

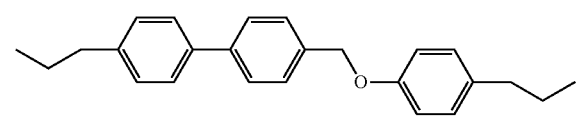

(101)

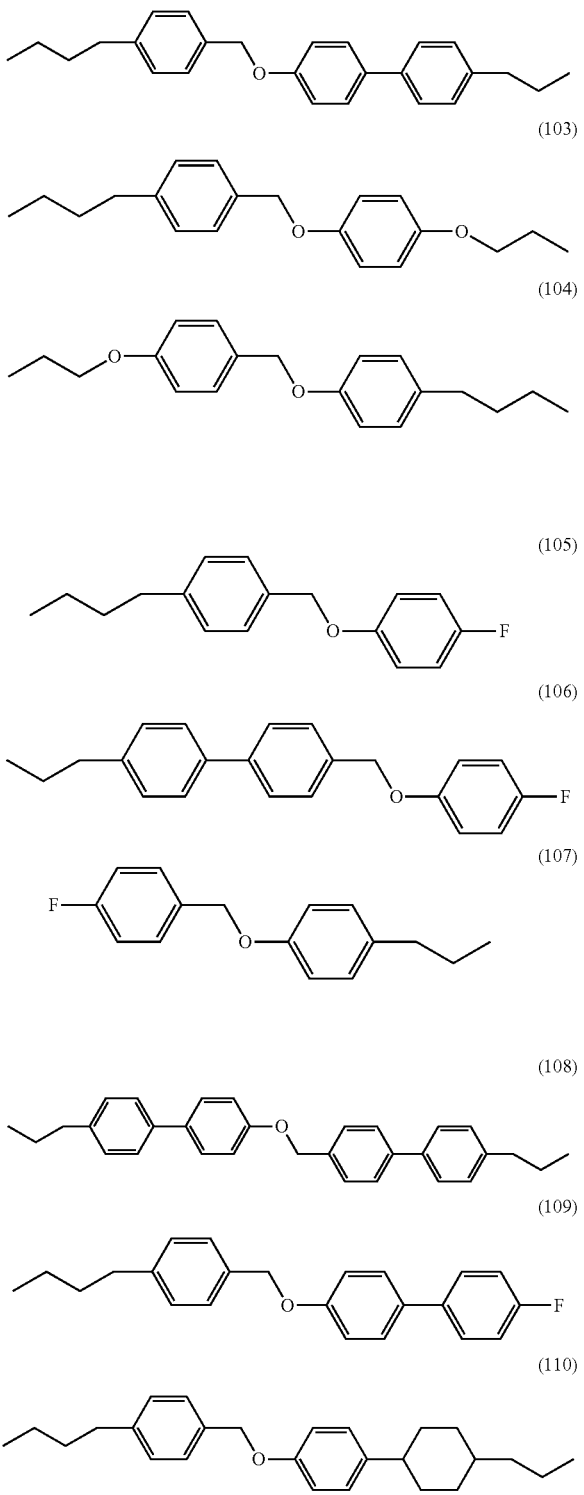

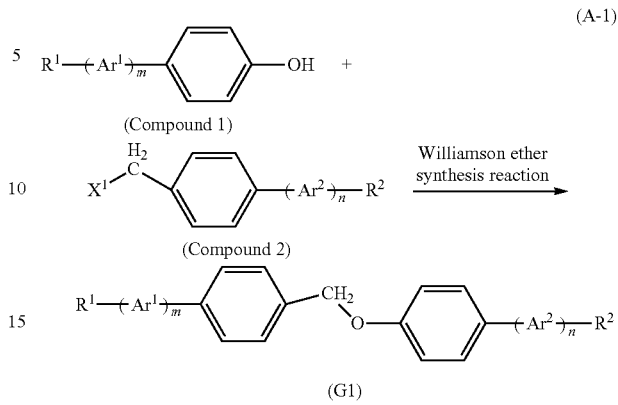

As shown in Synthesis Scheme (A-1), a hydroxyl group of Compound 1 is substituted with an alkoxy group through the Williamson ether synthesis reaction using an organic halide (Compound 2); thus, the biphenyl derivative represented by General Formula (G1) of one embodiment of the present invention can be synthesized.

In Synthesis Scheme (A-1), $Ar^1$ and $Ar^2$ separately represent a substituted or unsubstituted arylene group having 6 to 12 carbon atoms, a substituted or unsubstituted cycloalkylene group having 3 to 12 carbon atoms, or a substituted or unsubstituted cycloalkenylene group having 3 to 12 carbon atoms. In addition, m and n separately represent 0 or 1. $R^1$ and $R^2$ separately represent a hydrogen atom, a substituted or unsubstituted alkyl group having 1 to 11 carbon atoms, or a substituted or unsubstituted alkoxy group having 1 to 11 carbon atoms. Furthermore, $X^1$ represents either a halogen atom or a triflate group.

The organic compound of one embodiment of the present invention which is represented by General Formula (G1) and obtained in the above manner can be used as a material for a liquid crystal composition.

The liquid crystal composition of one embodiment of the present invention contains a liquid crystal compound, a non-liquid crystal compound, and/or a chiral material in addition to the organic compound represented by General Formula (G1).

The organic compound represented by General Formula (G1) has high resistivity. Furthermore, the liquid crystal composition of one embodiment of the present invention contains the organic compound represented by General Formula (G1) and thus has high resistivity.

This embodiment can be implemented in appropriate combination with any of the structures described in the other embodiments.

Embodiment 2

In this embodiment, a liquid crystal element and a liquid crystal display device each using the organic compound represented by General Formula (G1) in Embodiment 1 or a liquid crystal composition containing the organic compound will be described with reference to drawings.

Figure 1B:
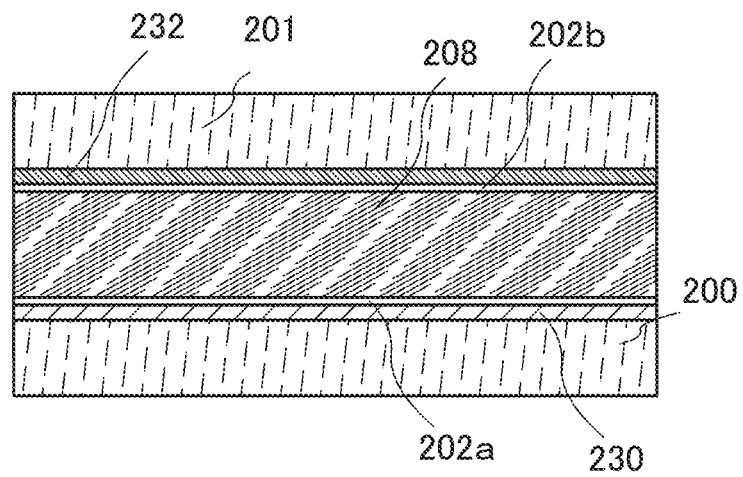

FIGS. 1A and 1B each illustrate examples of a liquid crystal element and a liquid crystal display device which are embodiments of the present invention.

Note that in this specification and the like, a liquid crystal element is an element which controls transmission of light by an optical modulation action of liquid crystal and Various types of reactions can be used for synthesis of the organic compound of one embodiment of the present invention represented by General Formula (G1).

For example, the organic compound represented by General Formula (G1) can be synthesized under Synthesis Scheme (A-1).

includes at least a pair of electrodes and a liquid crystal layer interposed therebetween. The liquid crystal layer includes a liquid crystal composition.

FIGS. 1A and 1B each illustrate a liquid crystal display device in which a first substrate 200 and a second substrate 201 are positioned to face each other with a liquid crystal composition 208 interposed therebetween.

The liquid crystal element in this embodiment includes at least a pair of electrodes (a pixel electrode layer 230 and a common electrode layer 232 having different potentials), and the liquid crystal composition 208 containing the organic compound represented by General Formula (G1) in Embodiment 1 between the pair of electrodes.

Differences between the liquid crystal element and the liquid crystal display device in FIG. 1A and those in FIG. 1B are positions of the pixel electrode layer 230 and the common electrode layer 232 with respect to the liquid crystal composition 208.

In FIG. 1A, the pixel electrode layer 230 and the common electrode layer 232 are provided between the first substrate 200 and the liquid crystal composition 208 so as to be adjacent to each other. With the structure in FIG. 1A, a method in which the gray scale is controlled by generating an electric field substantially parallel to a substrate to move liquid crystal molecules in a plane parallel to the substrate can be used.

In FIG. 1B, the pixel electrode layer 230 and the common electrode layer 232 are provided on the first substrate 200 side and the second substrate 201 side respectively, with the liquid crystal composition 208 interposed therebetween. With the structure in FIG. 1B, a method in which the gray scale is controlled by generating an electric field substantially perpendicular to a substrate to move liquid crystal molecules in a plane perpendicular to the substrate can be used.

An alignment film 202a may be provided between the liquid crystal composition 208 and the pixel electrode layer 230, and an alignment film 202b may be provided between the liquid crystal composition 208 and the common electrode layer 232. A liquid crystal composition of one embodiment of the present invention can be used for liquid crystal elements with a variety of structures and liquid crystal display devices with a variety of display modes.

The maximum thickness (film thickness) of the liquid crystal composition 208 is preferably greater than or equal to 1 μm and less than or equal to 20 μm.

The liquid crystal composition 208 can be formed by a dispenser method (a dropping method) or an injection method by which liquid crystal is injected using capillary action or the like after the first substrate 200 and the second substrate 201 are attached to each other.

Although not illustrated in FIGS. 1A and 1B, an optical film such as a polarizing plate, a retardation plate, or an anti-reflection film, or the like is provided as appropriate. For example, circular polarization by the polarizing plate and the retardation plate may be used. In addition, a backlight or the like can be used as a light source.

In this specification, a substrate provided with a semiconductor element (e.g., a transistor) and a pixel electrode layer is referred to as an element substrate (a first substrate), and a substrate which faces the element substrate with a liquid crystal composition interposed therebetween is referred to as a counter substrate (a second substrate).

As the liquid crystal display device of one embodiment of the present invention, a transmissive liquid crystal display device in which display is performed by transmission of light from a light source, a reflective liquid crystal display device in which display is performed by reflection of incident light, or a transflective liquid crystal display device in which a transmissive type and a reflective type are combined can be provided.

In the case of the transmissive liquid crystal display device, a pixel electrode layer, a common electrode layer, a first substrate, a second substrate, and other components such as an insulating film and a conductive film, which are provided in a pixel region through which light is transmitted, have a property of transmitting light in the visible wavelength range. In the liquid crystal display device having the structure illustrated in FIG. 1A, it is preferable that the pixel electrode layer and the common electrode layer have a light-transmitting property; however, if an opening pattern is provided, a non-light-transmitting material such as a metal film may be used depending on the shape.

In the case of the reflective liquid crystal display device, a reflective component which reflects light transmitted through a liquid crystal composition (e.g., a reflective film or substrate) may be provided on the side opposite to the viewing side of the liquid crystal composition. A light-transmitting material may be used for a substrate, an insulating film, and a conductive film which are provided between the viewing side of the liquid crystal composition and the reflective component. Note that in this specification, a light-transmitting property refers to a property of transmitting at least light in the visible wavelength range. In the liquid crystal display device having the structure illustrated in FIG. 1B, the pixel electrode layer or the common electrode layer on the side opposite to the viewing side may have a light-reflecting property so that it can be used as a reflective component.

The pixel electrode layer 230 and the common electrode layer 232 can be formed with the use of one or more of the following: indium tin oxide (ITO), indium zinc oxide (IZO) obtained by mixing zinc oxide (ZnO) into indium oxide, a conductive material in which silicon oxide ($SiO_2$) is mixed into indium oxide, indium oxide containing tungsten oxide, indium zinc oxide containing tungsten oxide, indium oxide containing titanium oxide, and indium tin oxide containing titanium oxide; graphene; metals such as tungsten (W), molybdenum (Mo), zirconium (Zr), hafnium (Hf), vanadium (V), niobium (Nb), tantalum (Ta), chromium (Cr), cobalt (Co), nickel (Ni), titanium (Ti), platinum (Pt), aluminum (Al), copper (Cu), and silver (Ag); alloys thereof; and metal nitrides thereof.

As the first substrate 200 and the second substrate 201, a glass substrate made of barium borosilicate glass, aluminoborosilicate glass, or the like, a quartz substrate, a plastic substrate, or the like can be used.

A liquid crystal composition containing the organic compound represented by General Formula (G1), which is one embodiment of the present invention, has high resistivity. The use of the liquid crystal composition with high resistivity enables the liquid crystal element to have a high voltage holding ratio.

Furthermore, in a liquid crystal display device including an element with a high voltage holding ratio as a liquid crystal element, leakage of electrical charges through the liquid crystal element can be inhibited, which results in low power consumption or high contrast.

The structures, the methods, and the like described in this embodiment can be combined as appropriate with any of the structures, the methods, and the like described in the other embodiments.

Embodiment 3

As a liquid crystal display device of one embodiment of the present invention, a passive matrix liquid crystal display device and an active matrix liquid crystal display device can be provided. In this embodiment, an example of an active matrix liquid crystal display device of one embodiment of the present invention will be described with reference to FIGS. 2A to 2C.

Figure 2A:
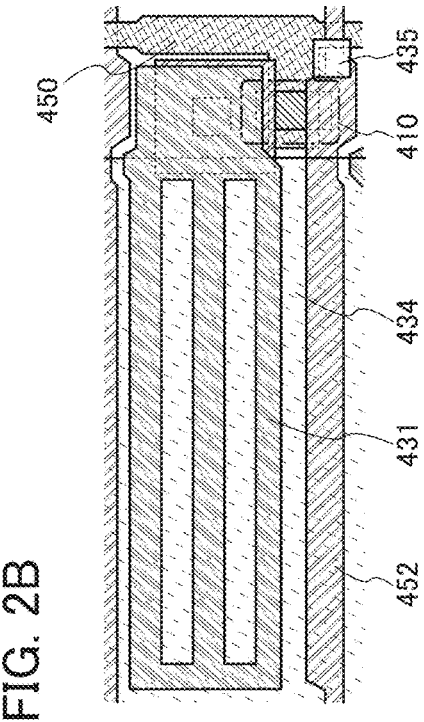
FIGS. 2A to 2C illustrate one mode of a liquid crystal display device.
Figure 2B:
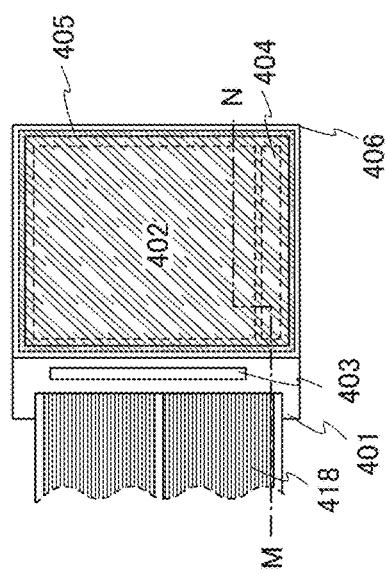
Figure 2C:
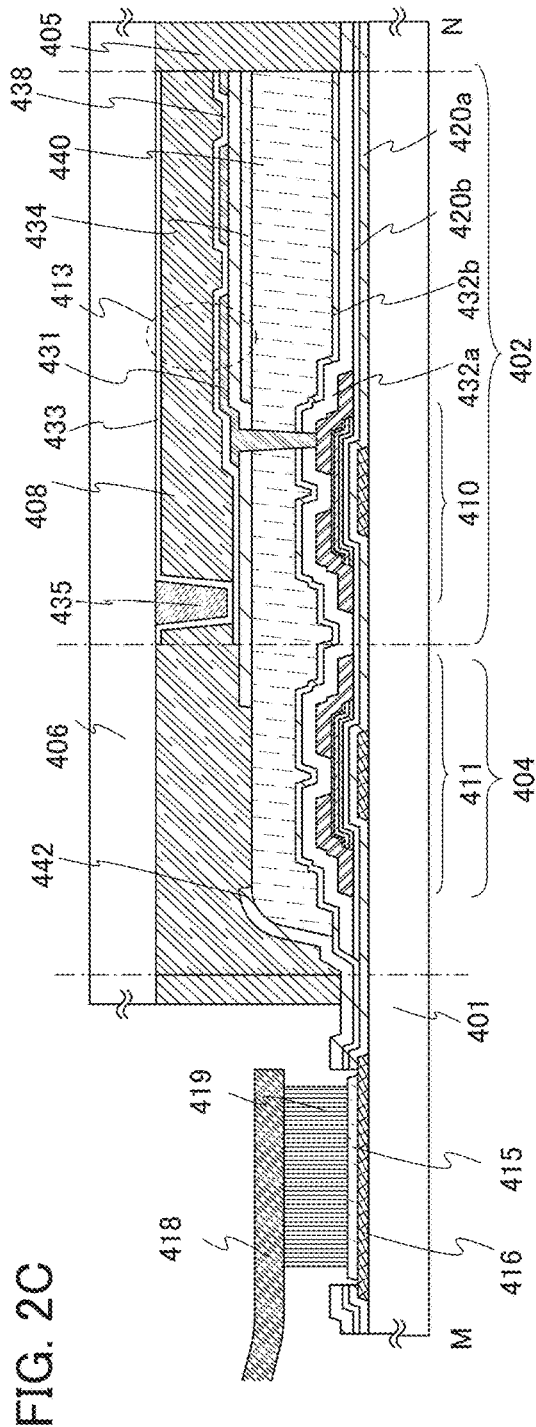

FIG. 2A is a plan view of the liquid crystal display device in this embodiment. FIG. 2B is a plan view of one pixel included in a display portion. FIG. 2C corresponds to a cross-sectional view taken along the line M-N in FIG. 2A.

In FIG. 2A, a sealant 405 is provided so as to surround a pixel portion 402 and a scan line driver circuit 404 which are provided over a substrate 401. A substrate 406 is provided over the pixel portion 402 and the scan line driver circuit 404. Consequently, the pixel portion 402 and the scan line driver circuit 404 are sealed together with a liquid crystal element by the substrate 401, the sealant 405, and the substrate 406.

In FIG. 2A, an IC chip is mounted on a region of the substrate 401, which is different from the region surrounded by the sealant 405; alternatively, a signal line driver circuit 403 formed using a single crystal semiconductor film or a polycrystalline semiconductor film is formed over a substrate separately prepared. Various signals and potentials applied to the pixel portion 402 through the signal line driver circuit 403 and the scan line driver circuit 404 are supplied from a flexible printed circuit (FPC) 418.

Although FIG. 2A illustrates an example in which the signal line driver circuit 403 is formed separately and mounted on the substrate 401, one embodiment of the present invention is not limited to this structure. The scan line driver circuit may be separately formed and then mounted, or only part of the signal line driver circuit or part of the scan line driver circuit may be separately formed and then mounted.

Note that there is no particular limitation on a method for connecting a separately formed driver circuit, and a chip on glass (COG) method, a wire bonding method, a tape automated bonding (TAB) method, or the like can be used. FIG. 2A illustrates an example in which the signal line driver circuit 403 is mounted by the COG method.

The pixel portion and the scan line driver circuit provided over the substrate include a plurality of transistors. As the transistors, a transistor in which a channel is formed in an oxide semiconductor is preferably used.

An oxide semiconductor has a wide energy gap of 3.0 eV or more. A transistor using an oxide semiconductor film obtained by processing an oxide semiconductor in an appropriate condition while sufficiently reducing the carrier density can have much lower leakage current between a source and a drain in an off state (off-state current) than a conventional transistor using silicon.

In this embodiment, the off-state current of transistors 410 and 411 used in the liquid crystal display device, in particular, the off-state current of the transistor 410 used in the pixel portion is preferably as low as possible, and specifically, the off-state current per micrometer of channel length is preferably lower than or equal to 100 zA. Since the off-state current is preferably as low as possible, the normalized off-state current is preferably lower than or equal to 10 zA/μm, more preferably lower than or equal to 1 zA/μm, still more preferably lower than or equal to 10 yA/μm.

By reducing impurities serving as electron donors, such as moisture or hydrogen, and also reducing oxygen vacancies, an i-type (intrinsic) or a substantially i-type oxide semiconductor can be obtained. Here, such an oxide semiconductor is referred to as a highly purified oxide semiconductor. When a highly purified oxide semiconductor is used for a channel, the normalized off-state current can be reduced to about several yoctoamperes per micrometer (yA/μm) to several zeptoamperes per micrometer (zA/μm).

An oxide semiconductor that can be used preferably contains at least indium (In) or zinc (Zn). In particular, In and Zn are preferably contained. In addition, as a stabilizer for reducing variations in electrical characteristics of transistors each using the oxide semiconductor, one or more elements selected from gallium (Ga), tin (Sn), hafnium (Hf), zirconium (Zr), titanium (Ti), scandium (Sc), yttrium (Y), and a lanthanoid (such as cerium (Ce), neodymium (Nd), or gadolinium (Gd)) are preferably contained. The transistor using the oxide semiconductor will be described in detail in Embodiment 4.

The transistors 410 and 411 are bottom-gate transistors in FIG. 2C; however, the transistors 410 and 411 in this embodiment are not limited thereto, and may be top-gate transistors. Alternatively, the transistors 410 and 411 may be dual-gate transistors each including two gate electrodes with a channel sandwiched therebetween. When the transistors 410 and 411 each including an oxide semiconductor are the dual-gate transistors, current drive characteristics can be improved and/or a change in the threshold voltage can be suppressed.

The liquid crystal display device of one embodiment of the present invention can employ a vertical electric field mode or a horizontal electric field mode. FIG. 2C illustrates an example in which a fringe field switching (FFS) mode is employed.

As illustrated in FIGS. 2A and 2C, the liquid crystal display device includes a connection terminal electrode 415 and a terminal electrode 416. The connection terminal electrode 415 and the terminal electrode 416 are electrically connected to a terminal included in the FPC 418 through an anisotropic conductive layer 419.

The connection terminal electrode 415 is formed from the same conductive layer as a first electrode layer 434. The terminal electrode 416 is formed from the same conductive layer as gate electrode layers of the transistors 410 and 411.

Insulating layers 432a and 432b are provided over the transistors 410 and 411.

In FIG. 2C, a planarization insulating layer 440 is provided over the insulating layer 432b, and an insulating layer 442 is provided between the first electrode layer 434 and a second electrode layer 431.

A gate insulating layer included in each of the transistors 410 and 411 can have a single layer structure or a stacked-layer structure. In this embodiment, the gate insulating layer may have a stacked-layer structure including gate insulating layers 420a and 420b. In FIG. 2C, the gate insulating layer 420a and the insulating layer 432b extend below the sealant 405 to cover an end portion of the terminal electrode 416, and the insulating layer 432b covers side surfaces of the gate insulating layer 420b and the insulating layer 432a.

The planarization insulating layer 440 can be formed using an organic resin such as an acrylic resin, a polyimide resin, a benzocyclobutene-based resin, a polyamide resin, or an epoxy resin. Other than such organic materials, a low-dielectric constant material (a low-k material), a siloxane-based resin, or the like can be used.

In FIG. 2C, a liquid crystal element 413 includes the first electrode layer 434, the second electrode layer 431, and a liquid crystal layer 408. The liquid crystal layer 408 is formed using a liquid crystal composition containing the organic compound represented by General Formula (G1) in Embodiment 1. Insulating layers 438 and 433 serving as alignment films are provided so that the liquid crystal layer 408 is interposed therebetween.

In the liquid crystal element 413, the second electrode layer 431 having an opening pattern is provided below the liquid crystal layer 408, and the first electrode layer 434 having a flat plate shape is provided below the second electrode layer 431 with the insulating layer 442 provided therebetween. The second electrode layer 431 having the opening pattern has a shape including a bend portion or a branching comb-like shape. Since the second electrode layer 431 has the opening pattern, an electric field can be generated between the first electrode layer 434 and the second electrode layer 431. Note that a structure may be employed in which the second electrode layer 431 having a flat plate shape is formed on and in contact with the planarization insulating layer 440, and the first electrode layer 434 having an opening pattern and serving as a pixel electrode is formed over the second electrode layer 431 with the insulating layer 442 provided therebetween.

The first electrode layer 434 and the second electrode layer 431 can be formed using a light-transmitting conductive material such as indium oxide containing tungsten oxide, indium zinc oxide containing tungsten oxide, indium oxide containing titanium oxide, indium tin oxide containing titanium oxide, indium tin oxide, indium zinc oxide, indium tin oxide to which silicon oxide is added, or graphene.

Alternatively, the first electrode layer 434 and the second electrode layer 431 can be formed using one or more materials selected from metals such as tungsten (W), molybdenum (Mo), zirconium (Zr), hafnium (Hf), vanadium (V), niobium (Nb), tantalum (Ta), chromium (Cr), cobalt (Co), nickel (Ni), titanium (Ti), platinum (Pt), aluminum (Al), copper (Cu), and silver (Ag); an alloy of any of these metals; and a nitride of any of these metals.

A conductive composition containing a conductive high molecule (also referred to as conductive polymer) can be used for the first electrode layer 434 and the second electrode layer 431.

A columnar spacer 435 is obtained by selective etching of an insulating layer and is provided to control the thickness (cell gap) of the liquid crystal layer 408. Alternatively, a spherical spacer may be used.

The size of a storage capacitor provided in the liquid crystal display device is set in consideration of the leakage current of the transistor provided in the pixel portion or the like so that electrical charges can be held for a predetermined period. The size of the storage capacitor may be set in consideration of the off-state current of the transistor or the like. In the liquid crystal display device described in this embodiment, leakage of electrical charges through the liquid crystal element can be inhibited because the liquid crystal element has a high voltage holding ratio; thus, the size of the storage capacitor can be small. In addition, the use of the transistor including an oxide semiconductor as a transistor can also contributes to a reduction of the size of the storage capacitor. Accordingly, the aperture ratio of each pixel can be improved, resulting in an increase in resolution.

In particular, it is preferable that a capacitor as a storage capacitor be not provided and that parasitic capacitance generated between the first electrode layer 434 and the second electrode layer 431 be used as a storage capacitor. Without the capacitor, the aperture ratio of the pixel can be further increased.

FIG. 2B illustrates an example of a pixel structure in which the capacitor as a storage capacitor is not provided for a pixel. The pixel includes an intersection portion of a wiring 450 electrically connected to the gate electrode layer of the transistor 410 and a wiring 452 electrically connected to one of a source electrode layer and a drain electrode layer of the transistor 410. Since the pixel in FIG. 2B does not include the capacitor as a storage capacitor, the ratio of the area of the second electrode layer 431 having the opening pattern to the area occupied by the pixel can be made large, and an extremely high aperture ratio can be obtained.

As described above, in the transistor using an oxide semiconductor, the current in an off state (off-state current) can be made low. Accordingly, an electric signal such as an image signal can be held for a longer period and a writing interval can be set longer.

With the use of a transistor with low off-state current, the liquid crystal display device in this embodiment can display images by at least two driving methods (modes). The first driving mode is a conventional driving method of a liquid crystal display device, in which data is rewritten sequentially every frame. The second driving mode is a driving method in which data rewriting is stopped after data writing is executed, i.e., a driving mode with a reduced refresh rate.

Moving images are displayed in the first driving mode. A still image can be displayed without change in image data every frame; thus, it is not necessary to rewrite data every frame. When the liquid crystal display device is driven in the second driving mode in displaying still images, power consumption can be reduced with less screen flicker.

In addition, since the liquid crystal element used in the liquid crystal display device of this embodiment has a high voltage holding ratio, leakage of electrical charges through the liquid crystal element can be inhibited. For this reason, a change in voltage applied to the liquid crystal layer can be inhibited for a long time even when the liquid crystal display device is used in the driving mode with a reduced refresh rate. This makes it possible to prevent screen flickers from being perceived by a user more effectively. Thus, the power consumption can be reduced and the display quality can be improved.

Note that in the liquid crystal display device of one embodiment of the present invention, a black matrix (light-blocking layer); an optical member (an optical substrate) such as a polarizing member, a retardation member, or an anti-reflection member; and the like are provided as appropriate. For example, circular polarization may be employed using a polarizing plate or a retardation plate. In addition, a backlight, a sidelight, or the like may be used as a light source.

As a display method in the pixel portion, a progressive method, an interlace method, or the like can be employed. Color elements controlled in each pixel for color display are not limited to three colors: R, G, and B (which correspond to red, green, and blue, respectively). For example, R, G, B, and W (W corresponds to white); or R, G, B, and one or more of yellow, cyan, magenta, and the like can be used. Furthermore, the sizes of display regions may be different between respective dots of color elements. Note that the disclosed invention is not limited to the application to a display device for color display and the disclosed invention can also be applied to a display device for monochrome display.

In addition, the liquid crystal display device may be provided with a touch sensor. An electronic device or the like using a liquid crystal display device in which a touch sensor is provided to overlap with the pixel portion 402 can be operated more intuitively.

The structures, the methods, and the like described in this embodiment can be combined as appropriate with any of the structures, the methods, and the like described in the other embodiments.

Embodiment 4

In this embodiment, a transistor that includes an oxide semiconductor and that can be used for the liquid crystal display device of one embodiment of the present invention will be described.

As the oxide semiconductor used to form a channel of the transistor, any of the following can be used, for example: indium oxide, tin oxide, zinc oxide, In—Zn-based oxide, Sn—Zn-based oxide, Al—Zn-based oxide, Zn—Mg-based oxide, Sn—Mg-based oxide, In—Mg-based oxide, In—Ga-based oxide, In—Ga—Zn-based oxide, In—Al—Zn-based oxide, In—Sn—Zn-based oxide, Sn—Ga—Zn-based oxide, Al—Ga—Zn-based oxide, Sn—Al—Zn-based oxide, In—Hf—Zn-based oxide, In—Zr—Zn-based oxide, In—Ti—Zn-based oxide, In—Sc—Zn-based oxide, In—Y—Zn-based oxide, In—La—Zn-based oxide, In—Ce—Zn-based oxide, In—Pr—Zn—based oxide, In—Nd—Zn—based oxide, In—Sm—Zn—based oxide, In—Eu—Zn—based oxide, In—Gd—Zn—based oxide, In—Tb—Zn—based oxide, In—Dy—Zn—based oxide, In—Ho—Zn—based oxide, In—Er—Zn—based oxide, In—Tm—Zn—based oxide, In—Yb—Zn—based oxide, In—Lu—Zn—based oxide, In—Sn—Ga—Zn—based oxide, In—Hf—Ga—Zn-based oxide, In—Al—Ga—Zn-based oxide, In—Sn—Al—Zn-based oxide, In—Sn—Hf—Zn—based oxide, and In—Hf—Al—Zn-based oxide.

Here, an In—Ga—Zn-based oxide refers to an oxide containing In, Ga, and Zn as its main components and there is no particular limitation on the ratio of In to Ga and Zn. The In—Ga—Zn-based oxide may contain a metal element other than In, Ga, and Zn.

Alternatively, a material represented by $InMO_3(ZnO)_m$ (where m is larger than 0) may be used as the oxide semiconductor. Note that M represents one or more metal elements selected from Ga, Fe, Mn, and Co, or any of the above-described elements as a stabilizer. Still alternatively, as the oxide semiconductor, a material represented by $In_2SnO_5(ZnO)_n$ (where n is larger than 0) may be used.

For example, it is possible to use an In—Ga—Zn-based oxide with an atomic ratio of In:Ga:Zn=1:1:1, In:Ga:Zn=1:3:2, In:Ga:Zn=3:1:2, or In:Ga:Zn=2:1:3, or an oxide whose atomic ratio is in the neighborhood of the above compositions.

If the oxide semiconductor film contains a large amount of hydrogen, the hydrogen and the oxide semiconductor are bonded to each other, so that part of the hydrogen serves as a donor and causes generation of an electron which is a carrier. As a result, the threshold voltage of the transistor including the oxide semiconductor shifts in the negative direction. Therefore, after formation of the oxide semiconductor film, dehydration treatment (dehydrogenation treatment) is preferably performed to remove hydrogen or moisture from the oxide semiconductor film so that the oxide semiconductor film is highly purified to contain impurities as little as possible.

Note that oxygen in the oxide semiconductor film is also reduced by the dehydration treatment (dehydrogenation treatment) in some cases. Accordingly, it is preferable that oxygen be added to the oxide semiconductor film to fill oxygen vacancies increased by the dehydration treatment (dehydrogenation treatment). Here, treatment for supplying oxygen to the oxide semiconductor film may be expressed as oxygen adding treatment, and treatment for making the oxygen content of the oxide semiconductor film be in excess of that in the stoichiometric composition may be expressed as treatment for making an oxygen-excess state.

In this manner, hydrogen or moisture is removed from the oxide semiconductor film by the dehydration treatment (dehydrogenation treatment) and oxygen vacancies therein are filled by the oxygen adding treatment, so that the oxide semiconductor film can be an i-type (intrinsic) oxide semiconductor film or a substantially i-type (intrinsic) highly purified oxide semiconductor film which is extremely close to an i-type oxide semiconductor film. Note that "substantially intrinsic" means that the oxide semiconductor film includes extremely few (close to zero) carriers derived from a donor and has a carrier density of $1\times10^{17}/cm^3$ or lower, $1\times10^{16}/cm^3$ or lower, $1\times10^{15}/cm^3$ or lower, $1\times10^{14}/cm^3$ or lower, or $1\times10^{13}/cm^3$ or lower.

A structure of the oxide semiconductor film is described below.

An oxide semiconductor film is classified roughly into a single-crystal oxide semiconductor film and a non-single-crystal oxide semiconductor film. The non-single-crystal oxide semiconductor film includes any of an amorphous oxide semiconductor film, a microcrystalline oxide semiconductor film, a polycrystalline oxide semiconductor film, a c-axis aligned crystalline oxide semiconductor (CAAC-OS) film, and the like.

The amorphous oxide semiconductor film has disordered atomic arrangement and no crystalline component. A typical example thereof is an oxide semiconductor film in which no crystal part exists even in a microscopic region, and the whole of the film is amorphous.

The microcrystalline oxide semiconductor film includes a microcrystal (also referred to as nanocrystal) with a size greater than or equal to 1 nm and less than 10 nm, for example. Thus, the microcrystalline oxide semiconductor film has a higher degree of atomic order than the amorphous oxide semiconductor film. Hence, the density of defect states of the microcrystalline oxide semiconductor film is lower than that of the amorphous oxide semiconductor film.

The CAAC-OS film is an oxide semiconductor film including a plurality of crystal parts, and most of the crystal parts each fit inside a cube whose one side is less than 100 nm. Thus, there is a case where a crystal part included in the CAAC-OS film fits inside a cube whose one side is less than 10 nm, less than 5 nm, or less than 3 nm. The density of defect states of the CAAC-OS film is lower than that of the microcrystalline oxide semiconductor film. The CAAC-OS film is described in detail below.

In a transmission electron microscope (TEM) image of the CAAC-OS film, a boundary between crystal parts, that is, a grain boundary is not clearly observed. Thus, in the CAAC-OS film, a reduction in electron mobility due to the grain boundary is less likely to occur.

According to the TEM image of the CAAC-OS film observed in a direction substantially parallel to a sample surface (cross-sectional TEM image), metal atoms are arranged in a layered manner in the crystal parts. Each metal atom layer has a morphology reflected by a surface over which the CAAC-OS film is formed (hereinafter, a surface over which the CAAC-OS film is formed is referred to as a formation surface) or a top surface of the CAAC-OS film, and is arranged in parallel to the formation surface or the top surface of the CAAC-OS film.

On the other hand, according to the TEM image of the CAAC-OS film observed in a direction substantially perpendicular to the sample surface (plan TEM image), metal atoms are arranged in a triangular or hexagonal configuration in the crystal parts. However, there is no regularity of arrangement of metal atoms between different crystal parts.

From the results of the cross-sectional TEM image and the plan TEM image, alignment is found in the crystal parts in the CAAC-OS film.

A CAAC-OS film is subjected to structural analysis with an X-ray diffraction (XRD) apparatus. For example, when the CAAC-OS film including an InGaZnO$_4$ crystal is analyzed by an out-of-plane method, a peak appears frequently when the diffraction angle (2θ) is around 31°. This peak is derived from the (009) plane of the InGaZnO$_4$ crystal, which indicates that crystals in the CAAC-OS film have c-axis alignment, and that the c-axes are aligned in a direction substantially perpendicular to the formation surface or the top surface of the CAAC-OS film.

On the other hand, when the CAAC-OS film is analyzed by an in-plane method in which an X-ray enters a sample in a direction substantially perpendicular to the c-axis, a peak appears frequently when 2θ is around 56°. This peak is derived from the (110) plane of the InGaZnO$_4$ crystal. Here, analysis (ϕ scan) is performed under conditions where the sample is rotated around a normal vector of a sample surface as an axis (ϕ axis) with 2θ fixed at around 56°. In the case where the sample is a single-crystal oxide semiconductor film of InGaZnO$_4$, six peaks appear. The six peaks are derived from crystal planes equivalent to the (110) plane. On the other hand, in the case of a CAAC-OS film, a peak is not clearly observed even when ϕ scan is performed with 2θ fixed at around 56°.

According to the above results, in the CAAC-OS film, while the directions of a-axes and b-axes are different between crystal parts, the c-axes are aligned in a direction parallel to a normal vector of a formation surface or a normal vector of a top surface. Thus, each metal atom layer arranged in a layered manner observed in the cross-sectional TEM image corresponds to a plane parallel to the a-b plane of the crystal.

Note that the crystal part is formed concurrently with deposition of the CAAC-OS film or is formed through crystallization treatment such as heat treatment. As described above, the c-axis of the crystal is aligned in a direction parallel to a normal vector of a formation surface or a normal vector of a top surface of the CAAC-OS film. Thus, for example, in the case where a shape of the CAAC-OS film is changed by etching or the like, the c-axis might not be necessarily parallel to a normal vector of a formation surface or a normal vector of a top surface of the CAAC-OS film.

Further, the degree of crystallinity in the CAAC-OS film is not necessarily uniform. For example, in the case where crystal growth leading to the CAAC-OS film occurs from the vicinity of the top surface of the film, the degree of the crystallinity in the vicinity of the top surface is higher than that in the vicinity of the formation surface in some cases. Further, when an impurity is added to the CAAC-OS film, the crystallinity in a region to which the impurity is added is changed, and the degree of crystallinity in the CAAC-OS film varies depending on the region.

Note that when the CAAC-OS film with an InGaZnO$_4$ crystal is analyzed by an out-of-plane method, a peak of 2θ may also be observed at around 36°, in addition to the peak of 2θ at around 31°. The peak of 2θ at around 36° indicates that a crystal having no c-axis alignment is included in part of the CAAC-OS film. It is preferable that in the CAAC-OS film, a peak of 2θ appears at around 31° and a peak of 2θ do not appear at around 36°.

With the use of the CAAC-OS film in a transistor, variation in electrical characteristics of the transistor due to irradiation with visible light or ultraviolet light is small. Thus, the transistor has high reliability.

Note that an oxide semiconductor film may be a stacked film including two or more kinds of an amorphous oxide semiconductor film, a microcrystalline oxide semiconductor film, and a CAAC-OS film, for example.

In this specification, the term "parallel" indicates that the angle formed between two straight lines ranges from −10° to 10°, and accordingly also includes the case where the angle ranges from −5° to 5°. In addition, the term "perpendicular" indicates that the angle formed between two straight lines ranges from 80° to 100°, and accordingly includes the case where the angle ranges from 85° to 95°.

In this specification, the trigonal and rhombohedral crystal systems are included in the hexagonal crystal system.

The structures, the methods, and the like described in this embodiment can be combined as appropriate with any of the structures, the methods, and the like described in the other embodiments.

Embodiment 5

In this embodiment, the significance of a reduction in refresh rate described in the above embodiments is explained.

The eye strain is divided into two categories: nerve strain and muscle strain. The nerve strain is caused by prolonged looking at light emitted from a liquid crystal display device or blinking images. This is because the brightness stimulates and fatigues the retina and nerve of the eye and the brain. The muscle strain is caused by overuse of a ciliary muscle which works for adjusting the focus.

Figure 3A:
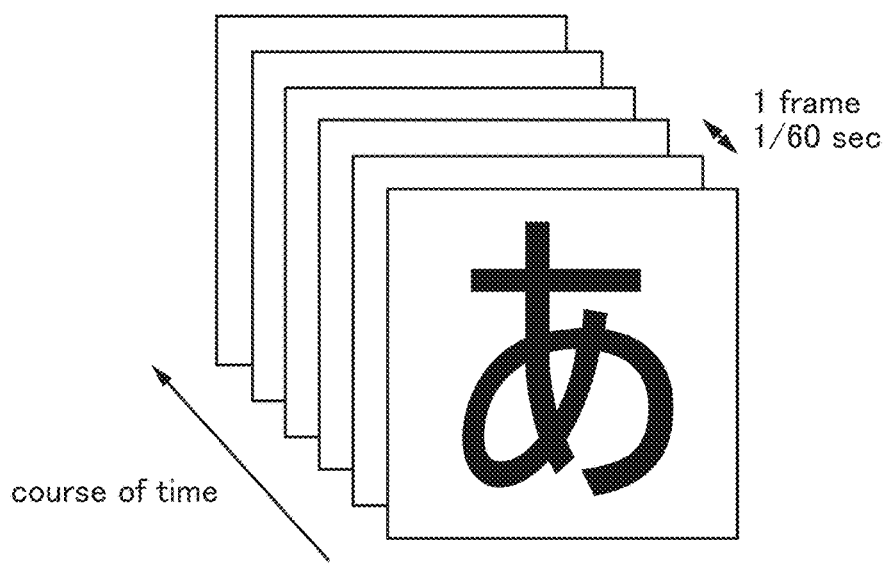
FIGS. 3A and 3B are schematic diagrams illustrating examples of a driving method of a liquid crystal display device.

FIG. 3A is a schematic diagram illustrating display of a conventional liquid crystal display device. As illustrated in FIG. 3A, for the display of the conventional liquid crystal display device, image rewriting is performed 60 times per second. A prolonged looking at such a screen might stimulate the retina and nerve of the eye and the brain of a user and lead to eye strain.

In one embodiment of the present invention, a transistor with an extremely low off-state current (e.g., a transistor using an oxide semiconductor) is used in a pixel portion of a liquid crystal display device. As a liquid crystal element, a liquid crystal element with a high voltage holding ratio is used. With these components, leakage of electrical charges applied to a liquid crystal layer can be inhibited, whereby the luminance of a liquid crystal display device can be kept even at a lower frame frequency.

Figure 3B:
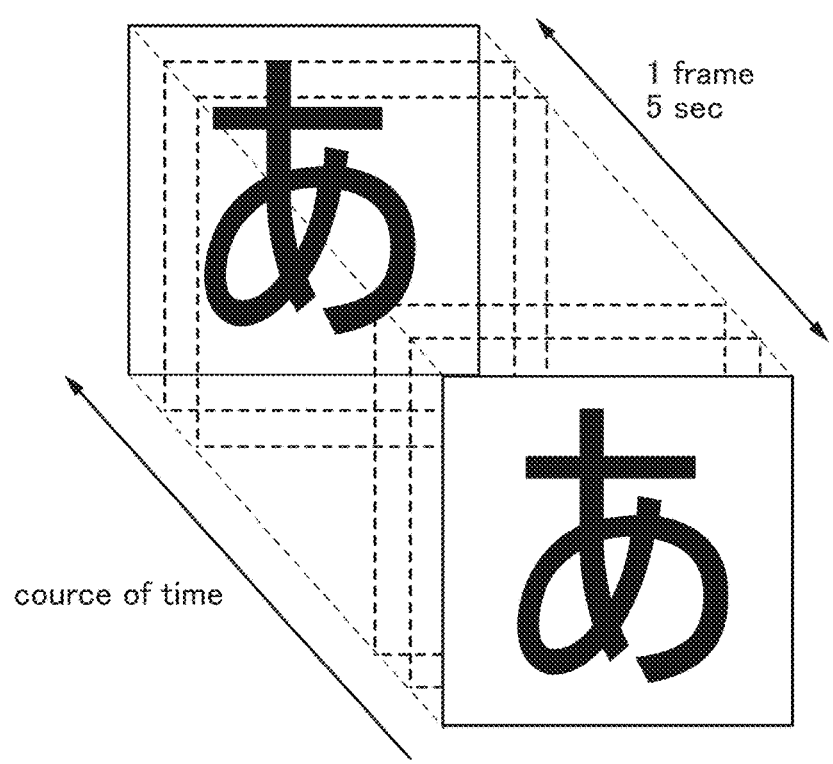

Thus, for example, the number of times of image writing can be reduced to once every five seconds as illustrated in FIG. 3B. The same image can be displayed for as long as possible and flickers on a screen perceived by a user can be reduced. This makes it possible to reduce stimuli to the retina and nerve of the eye and the brain of a user, resulting in less nerve strain.

Figure 4A:
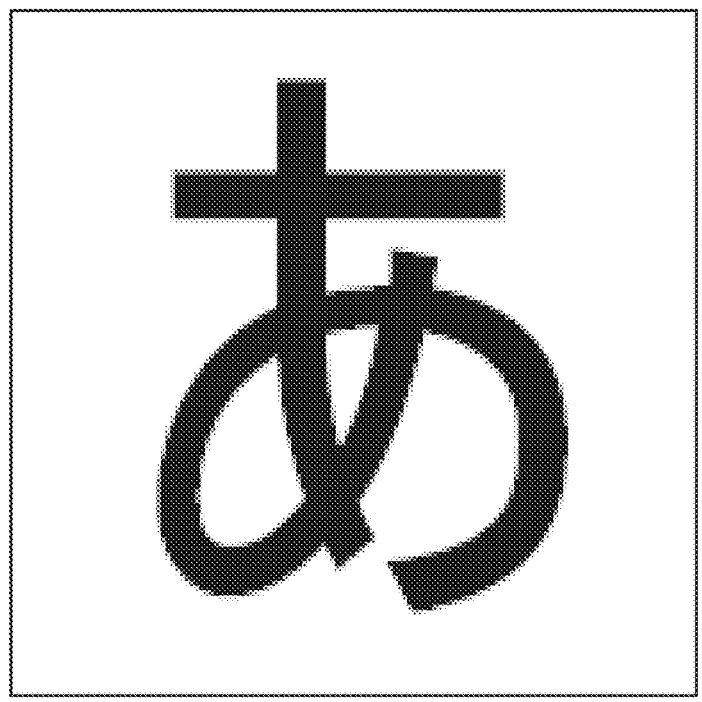
FIGS. 4A and 4B are schematic diagrams illustrating examples of a driving method of a liquid crystal display device.

In the case where the size of one pixel is large (e.g., the resolution is less than 150 ppi), a blurred character is displayed by a liquid crystal display device as illustrated in FIG. 4A. When a user looks at the blurred character displayed on the liquid crystal display device for a long time, his/her ciliary muscle keeps working to adjust the focus in a state where adjusting the focus is difficult, which might lead to eye strain.

Figure 4B:
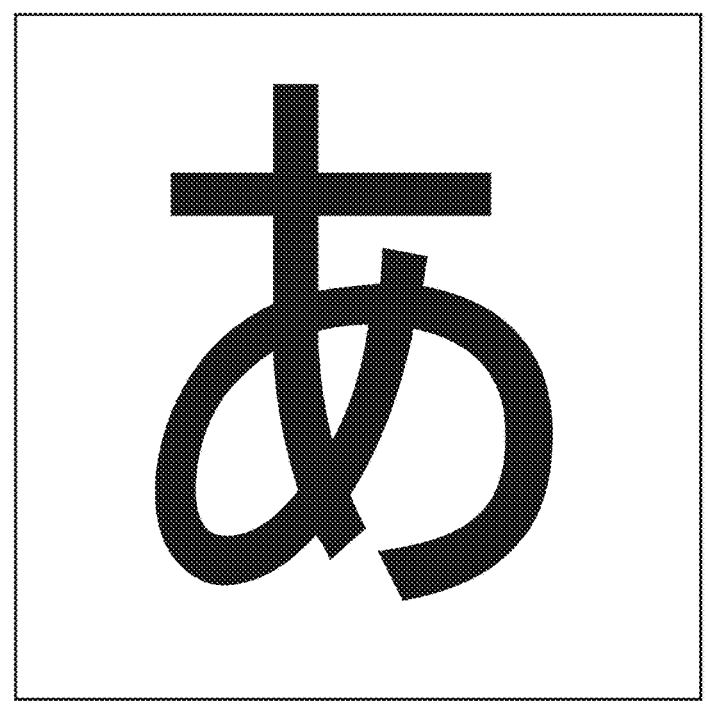

In contrast, in the liquid crystal display device of one embodiment of the present invention, the size of one pixel is small and thus high resolution display is performed as illustrated in FIG. 4B, so that precise and smooth display can be achieved. The precise and smooth display enables ciliary muscles to adjust the focus more easily, and reduces muscle strain of a user.

Quantitative measurement of eye strain has been studied. For example, the critical flicker (fusion) frequency (CFF) is known as an index of measuring nerve strain; and the accommodation time and the accommodation near point are known as indexes of measuring muscle strain.

Examples of other methods for measuring eye strain include electroencephalography, thermography, measurement of the number of blinkings, measurement of tear volume, measurement of a pupil contractile response speed, and a questionnaire for surveying subjective symptoms.

One embodiment of the present invention can provide an eye-friendly liquid crystal display device.

Embodiment 6

A liquid crystal display device disclosed in this specification can be applied to a variety of electronic devices (including game machines). Examples of electronic devices are a television set (also referred to as a television or a television receiver), a monitor of a computer or the like, a camera such as a digital camera or a digital video camera, a digital photo frame, a mobile phone handset (also referred to as a mobile phone or a mobile phone device), a portable game machine, a portable information terminal, an audio reproducing device, a large-sized game machine such as a pachinko machine, and the like.

Figure 5A:
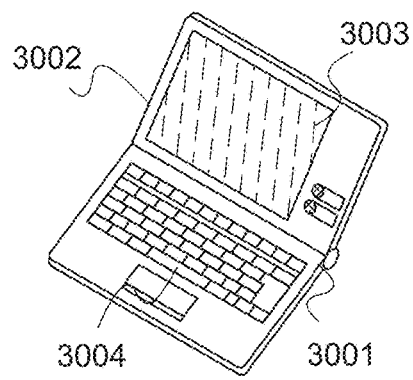
FIGS. 5A to 5F each illustrate one mode of an electronic device.

FIG. 5A illustrates a laptop personal computer, which includes a main body 3001, a housing 3002, a display portion 3003, a keyboard 3004, and the like. The liquid crystal display device described in any of the above embodiments is used for the display portion 3003, whereby low voltage driving and a reduction in power consumption of the laptop personal computer can be achieved.

Figure 5B:
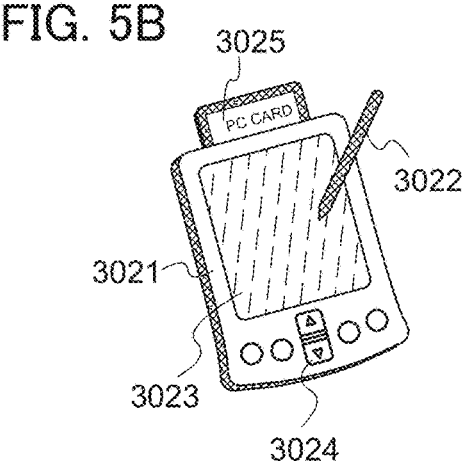

FIG. 5B illustrates a personal digital assistant (PDA), which includes a main body 3021 provided with a display portion 3023, an external interface 3025, operation buttons 3024, and the like. A stylus 3022 is provided as an accessory for operation. The liquid crystal display device described in any of the above embodiments is used for the display portion 3023, whereby low voltage driving and a reduction in power consumption of the personal digital assistant (PDA) can be achieved.

Figure 5C:
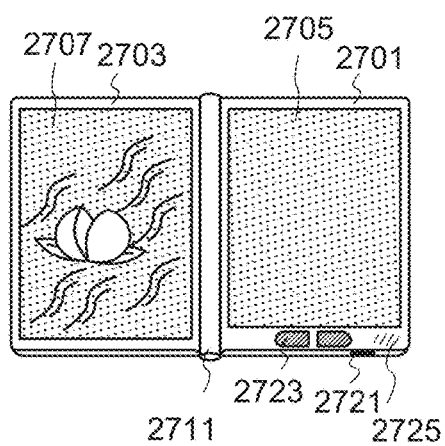

FIG. 5C illustrates an e-book reader, which includes two housings, a housing 2701 and a housing 2703. The housing 2701 and the housing 2703 are combined with a hinge 2711 so that the e-book reader can be opened and closed with the hinge 2711 as an axis. With such a structure, the e-book reader can operate like a paper book.

A display portion 2705 and a display portion 2707 are incorporated in the housing 2701 and the housing 2703, respectively. The display portion 2705 and the display portion 2707 may display one image or different images. In the structure where different images are displayed in the above display portions, for example, the right display portion (the display portion 2705 in FIG. 5C) can display text and the left display portion (the display portion 2707 in FIG. 5C) can display images. The liquid crystal display device described in any of the above embodiments is used for the display portions 2705 and 2707, whereby low voltage driving and a reduction in power consumption of the e-book reader can be achieved. In the case of using a transflective or reflective liquid crystal display device as the display portion 2705, the e-book reader may be used in a comparatively bright environment; therefore, a solar cell may be provided so that power generation by the solar cell and charge of a battery can be performed. When a lithium ion battery is used as the battery, there are advantages of downsizing and the like.

FIG. 5C illustrates an example in which the housing 2701 is provided with an operation portion and the like. For example, the housing 2701 is provided with a power switch 2721, operation keys 2723, a speaker 2725, and the like. With the operation keys 2723, pages can be turned. Note that a keyboard, a pointing device, or the like may also be provided on the surface of the housing, on which the display portion is provided. Furthermore, an external connection terminal (an earphone terminal, a USB terminal, or the like), a recording medium insertion portion, and the like may be provided on the back surface or the side surface of the housing. In addition, the e-book reader may have a function of an electronic dictionary.

The e-book reader may transmit and receive data wirelessly. Through wireless communication, desired book data or the like can be purchased and downloaded from an electronic book server.

Figure 5D:
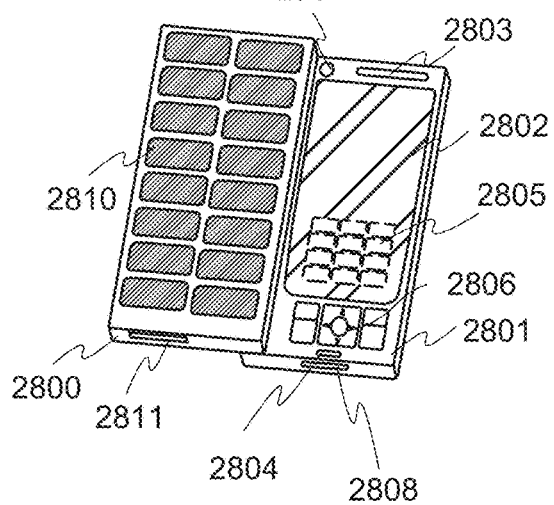

FIG. 5D illustrates a mobile phone, which includes two housings, a housing 2800 and a housing 2801. The housing 2801 includes a display panel 2802, a speaker 2803, a microphone 2804, a pointing device 2806, a camera lens 2807, an external connection terminal 2808, and the like. In addition, the housing 2800 includes a solar cell 2810 having a function of charge of the mobile phone, an external memory slot 2811, and the like. An antenna is incorporated in the housing 2801. The liquid crystal display device described in any of the above embodiments is used for the display panel 2802, whereby low voltage driving and a reduction in power consumption of the mobile phone can be achieved.

Further, the display panel 2802 is provided with a touch panel. A plurality of operation keys 2805 which is displayed as images is illustrated by dotted lines in FIG. 5D. Note that a boosting circuit by which a voltage output from the solar cell 2810 is increased to be sufficiently high for each circuit is also provided.

The display direction of the display panel 2802 is changed as appropriate depending on a usage pattern. The camera lens 2807 is provided on the same surface as the display panel 2802, so that the mobile phone can be used as a video phone. The speaker 2803 and the microphone 2804 can be used for videophone calls, recording and playing sound, and the like as well as voice calls. Furthermore, the housings 2800 and 2801 which are developed as illustrated in FIG. 5D can overlap with each other by sliding; thus, the size of the mobile phone can be decreased, which makes the mobile phone suitable for being carried.

The external connection terminal 2808 can be connected to an AC adapter and various types of cables such as a USB cable, and charge and data communication with a personal computer are possible. Moreover, a large amount of data can be stored by inserting a storage medium into the external memory slot 2811 and can be moved.

Further, in addition to the above functions, an infrared communication function, a television reception function, or the like may be provided.

Figure 5E:
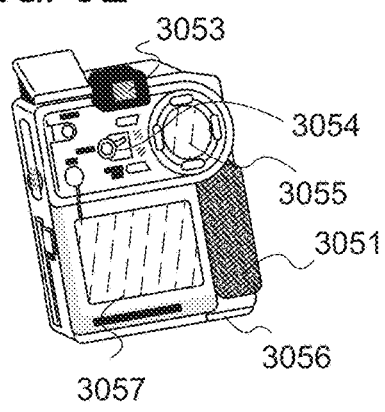

FIG. 5E illustrates a digital video camera, which includes a main body 3051, a display portion A 3057, an eyepiece 3053, an operation switch 3054, a display portion B 3055, a battery 3056, and the like. The liquid crystal display device described in any of the above embodiments is used for the display portion A 3057 and the display portion B 3055, whereby low voltage driving and a reduction in power consumption of the digital video camera can be achieved.

Figure 5F:
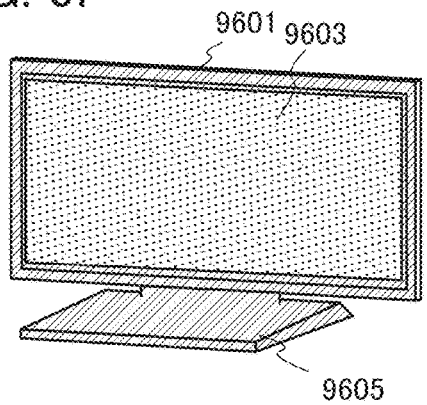

FIG. 5F illustrates a television set, which includes a housing 9601, a display portion 9603, and the like. The display portion 9603 can display images. Here, the housing 9601 is supported by a stand 9605. The liquid crystal display device described in any of the above embodiments is used for the display portion 9603, whereby low voltage driving and a reduction in power consumption of the television set can be achieved.

The television set can operate with an operation switch of the housing 9601 or a separate remote controller. Further, the remote controller may be provided with a display portion for displaying data output from the remote controller.

Note that the television set is provided with a receiver, a modem, and the like. With the use of the receiver, general television broadcasting can be received. Moreover, when the television set is connected to a communication network with or without wires via the modem, one-way (from a sender to a receiver) or two-way (between a sender and a receiver or between receivers) data communication can be performed.

The structures, the methods, and the like described in this embodiment can be combined as appropriate with any of the structures, the methods, and the like described in the other embodiments.

Example 1

In this example, an example of synthesizing 4-n-propyl-4'-(4-n-propylphenoxy)methylbiphenyl (abbreviation: Dal-PPCH2OP-3) represented by Structural Formula (101) in Embodiment 1 will be described.

[Chemical Formula 5]

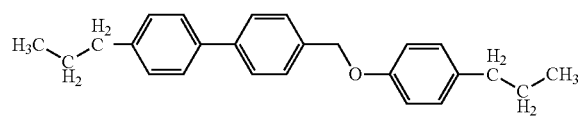

(101)

Step 1: Synthesis of 4-(4-n-propylphenyl)benzyl bromide

In a flask were put 6.2 g (21 mmol) of 4-iodobenzyl bromide, 3.4 g (21 mmol) of 4-n-propylphenylboronic acid, 0.32 g (1.0 mmol) of tri(o-tolyl)phosphine, 52 mL of toluene, 52 mL of ethanol, and 21 mL of a 2M aqueous solution of potassium carbonate. The mixture was degassed while being stirred under reduced pressure, and the atmosphere in the flask was replaced with nitrogen after the degassing. Then, 47 mg (0.21 mmol) of palladium(II) acetate was added to this mixture, and the mixture was stirred at 90° C. for 1 hour.

Ethyl acetate and water were added to the obtained mixture to extract an organic layer, and an aqueous layer was subjected to extraction with ethyl acetate. The obtained extract solution and the organic layer were combined, washed with water and a saturated aqueous solution of sodium chloride, and then dried with magnesium sulfate. This mixture was separated by gravity filtration. The filtrate was concentrated and subjected to suction filtration through Celite (produced by Wako Pure Chemical Industries, Ltd., Catalog No. 531-16855), alumina, Florisil (produced by Wako Pure Chemical Industries, Ltd., Catalog No. 540-00135), and silica gel. The resulting filtrate was concentrated to give a light yellow solid.

This solid was purified by high performance liquid column chromatography (HPLC) (the developing solvent was chloroform). The obtained fraction was concentrated to give 1.2 g of a light yellow solid of 4-(4-n-propylphenyl)benzyl bromide, which was an objective substance, in a yield of 20%. The synthesis scheme of Step 1 is shown in (E1-1) below.

[Chemical Formula 6]

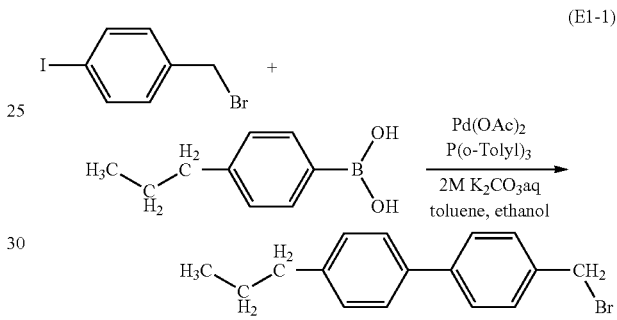

(E1-1)

Step 2: Synthesis of 4-n-propyl-4'-(4-n-propylphenoxy)methylbiphenyl

In a 200-mL recovery flask were put 1.2 g (4.2 mmol) of 4-(4-n-propylphenyl)benzyl bromide, 0.63 g (4.6 mmol) of 4-n-propylphenol, 0.64 g (4.6 mmol) of potassium carbonate, and 30 mL of acetone. The mixture was stirred at 60° C. in the air for 6 hours. Ethyl acetate and water were added to the obtained mixture to extract an organic layer, and an aqueous layer was subjected to extraction with ethyl acetate. The obtained extract solution and the organic layer were combined, washed with water and a saturated aqueous solution of sodium chloride, and then dried with magnesium sulfate. This mixture was separated by gravity filtration, and the filtrate was concentrated to give a light yellow solid.

This solid was purified by silica gel column chromatography (as the developing solvent, first, hexane was used, and then hexane and ethyl acetate in a ratio of 5:1 were used). The obtained fraction was concentrated to give a white solid. This solid was purified by HPLC (the developing solvent was chloroform). The obtained fraction was concentrated to give 0.46 g of a white solid, which was an objective substance, in a yield of 33%. By a train sublimation method, this solid was purified. In the purification by sublimation, the white solid was heated at 147° C. under a pressure of 2.4 Pa with a flow rate of argon of 10 mL/min. After the purification by sublimation, 0.30 g of a white solid of 4-n-propyl-4'-(4-n-propylphenoxy)methylbiphenyl, which was the objective substance, was obtained at a collection rate of 65%. The synthesis scheme of Step 2 is shown in (E1-2) below.

[Chemical Formula 7]

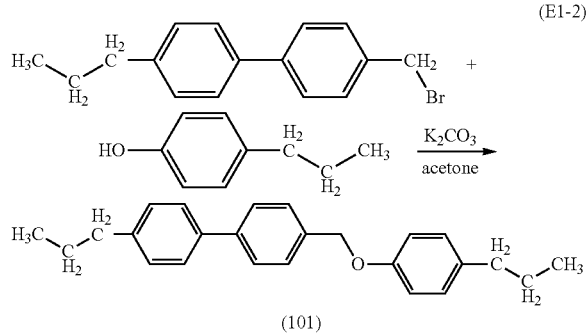

(E1-2)

(101)

This compound was identified as 4-n-propyl-4'-(4-n-propylphenoxy)methylbiphenyl (abbreviation: Dal-PPCH2OP-3), which was the objective substance, by nuclear magnetic resonance (NMR) spectroscopy.

Figure 6A:
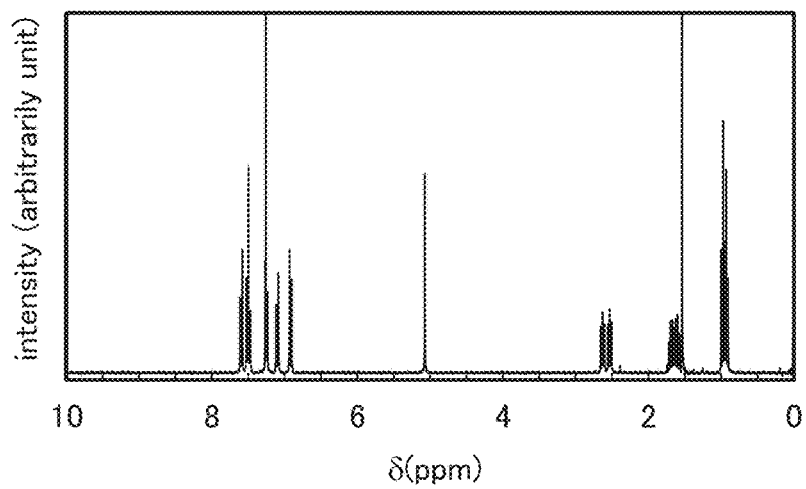
FIGS. 6A to 6C are $^1$H NMR charts of Dal-PPCH2OP-3.
Figure 6B:
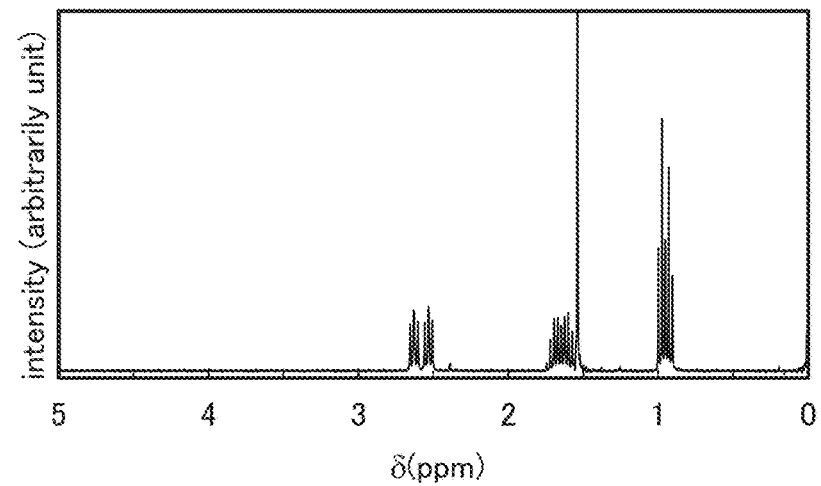
Figure 6C:
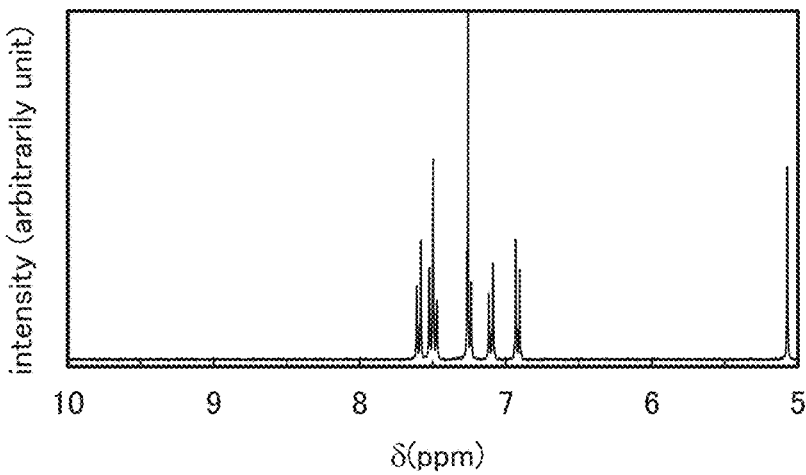

The $^1$H NMR data of Dal-PPCH2OP-3, the obtained substance, is shown below. FIGS. 6A to 6C show NMR charts. FIG. 6B is an enlarged chart showing a range of 0 ppm to 5.0 ppm in FIG. 6A. FIG. 6C is an enlarged chart showing a range of 5.0 ppm to 10 ppm in FIG. 6A.

$^1$H NMR (CDC$_3$, 300 MHz): δ (ppm)=0.91-1.00 (m, 6H), 1.56-1.75 (m, 4H), 2.53 (t, 2H), 2.63 (t, 2H), 5.07 (s, 2H), 6.92 (d, 2H), 7.10 (d, 2H), 7.25 (d, 2H), 7.50 (t, 4H), 7.60 (d, 2H).

Example 2

In this example, an example of synthesizing 4-(4-n-butylbenzyloxy)-4'-n-propylbiphenyl (abbreviation: Dal-PCH2OPP-4,3) represented by Structural Formula (102) in Embodiment 1 will be described.

[Chemical Formula 8]

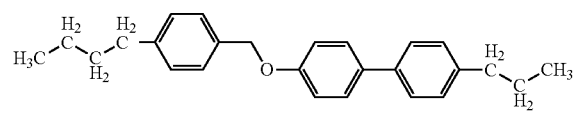

(102)

Step 1: Synthesis of 4-hydroxy-4'-n-propylbiphenyl

Into a flask were put 5.6 g (34 mmol) of 4-n-propylphenylbronic acid, 4.9 g (28 mmol) of 4-bromophenol, 0.43 g (1.4 mmol) of tris(2-methylphenyl)phosphine, 70 mL of toluene, 70 mL of ethanol, and 28 mL of a 2M aqueous solution of potassium carbonate. The mixture was degassed while being stirred under reduced pressure, and the air in the flask was replaced with nitrogen after the degassing. Then, 64 mg (0.28 mmol) of palladium(II) acetate was added to this mixture, and the mixture was stirred at 90° C. for 6.5 hours.

Ethyl acetate and water were added to the obtained mixture to extract an organic layer, and an aqueous layer was subjected to extraction with ethyl acetate. The obtained extract solution and the organic layer were combined, washed with water and a saturated aqueous solution of sodium chloride, and then dried with magnesium sulfate.

This mixture was separated by gravity filtration, and the filtrate was concentrated to give a white solid. Hexane was added to this solid, followed by irradiation with ultrasonic waves. The solid was separated by suction filtration. The obtained solid was recrystallized with toluene to give 4.3 g of a white solid of 4-hydroxy-4'-n-propylbiphenyl, which was an objective substance, in a yield of 71%. The synthesis scheme of Step 1 is shown in (E2-1) below.

[Chemical Formula 9]

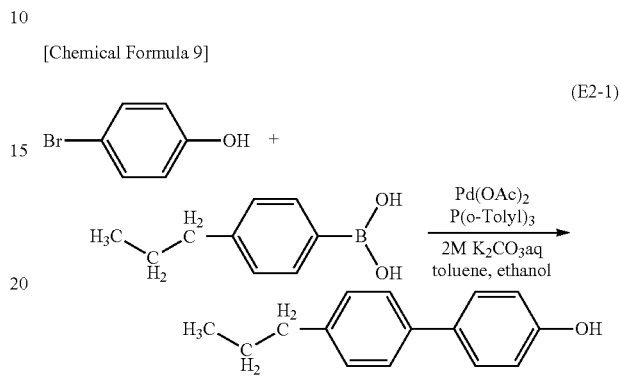

(E2-1)

Step 2: Synthesis of 4-(4-n-butylbenzyloxy)-4'-n-propylbiphenyl

In a 200-mL recovery flask were put 1.3 g (5.6 mmol) of 4-n-butylbenzyl bromide, 1.3 g (6.1 mmol) of 4-hydroxy-4'-n-propylbiphenyl, 0.85 g (6.1 mmol) of potassium carbonate, and 30 mL of acetone. The mixture was stirred at 60° C. in the air for 4 hours. Toluene and water were added to the obtained mixture to extract an organic layer, and an aqueous layer was subjected to extraction with toluene. The obtained extract solution and the organic layer were combined, washed with water and a saturated aqueous solution of sodium chloride, and then dried with magnesium sulfate. This mixture was separated by gravity filtration, and the filtrate was concentrated to give a white solid.

This solid was purified by silica gel column chromatography (the developing solvent was hexane). The obtained fraction was concentrated to give a white solid. This solid was purified by HPLC (the developing solvent was chloroform). The obtained fraction was concentrated to give 1.5 g of a white solid, which was an objective substance, in a yield of 75%. By a train sublimation method, this solid was purified. In the purification by sublimation, the white solid was heated at 175° C. under a pressure of 2.3 Pa with a flow rate of argon of 10 mL/min. After the purification by sublimation, 1.3 g of a white solid of 4-(4-n-butylbenzyloxy)-4'-n-propylbiphenyl, which was the objective substance, was obtained at a collection rate of 87%. The synthesis scheme of Step 2 is shown in (E2-2) below.

[Chemical Formula 10]

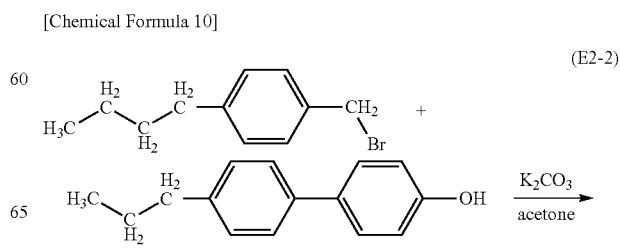

(E2-2)

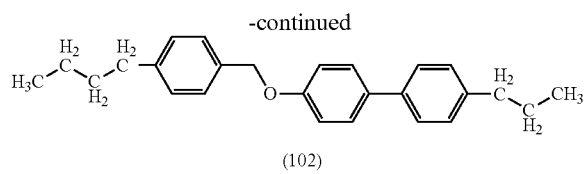

(102)

This compound was identified as 4-(4-n-butylbenzyloxy)-4'-n-propylbiphenyl (abbreviation: Dal-PCH2OPP-4,3), which was the objective substance, by NMR spectrometry.

Figure 7A:
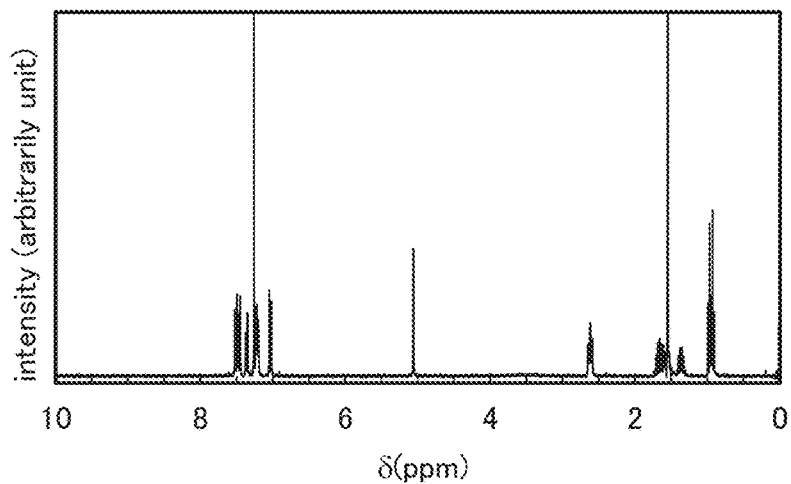
FIGS. 7A to 7C are $^1$H NMR charts of Dal-PCH2OPP-4,3.
Figure 7B:
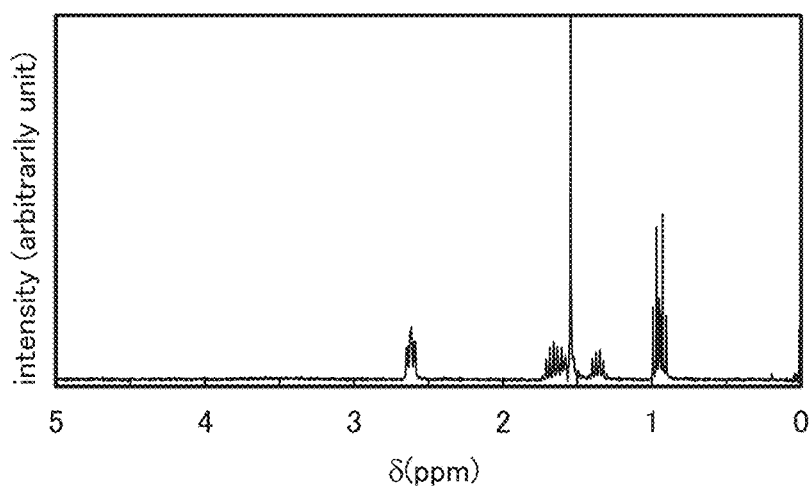
Figure 7C:
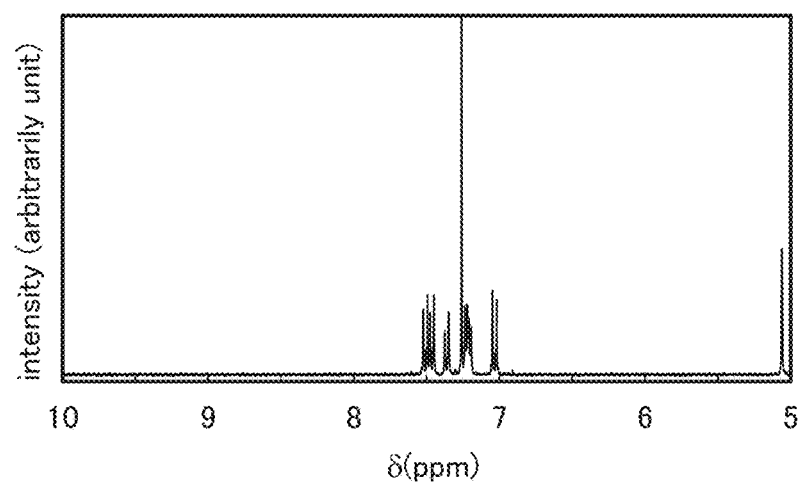

The $^1$H NMR data of Dal-PCH2OPP-4,3, the obtained substance, is shown below. FIGS. 7A to 7C show NMR charts. FIG. 7B is an enlarged chart showing a range of 0 ppm to 5.0 ppm in FIG. 7A. FIG. 7C is an enlarged chart showing a range of 5.0 ppm to 10 ppm in FIG. 7A.

$^1$H NMR (CDC$_3$, 300 MHz): δ (ppm)=0.91-0.99 (m, 6H), 1.33-1.40 (m, 2H), 1.55-1.71 (m, 4H), 2.59-2.65 (m, 4H), 5.06 (s, 2H), 7.03 (d, 2H), 7.19-7.24 (m, 4H), 7.36 (d, 2H), 7.45-7.52 (m, 4H).

Example 3

In this example, an example of synthesizing 1-(4-n-butylbenzyloxy)-4-(trans-4-n-propylcyclohexyl)benzene (abbreviation: Dal-PCH2OPC-4,3) represented by Structural Formula (110) in Embodiment 1 will be described.

[Chemical Formula 11]

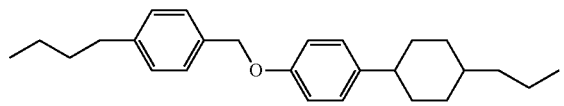

(110)

Step 1: Synthesis of 1-(4-n-butylbenzyloxy)-4-(trans-4-n-propylcyclohexyl)benzene In a 100-mL three-neck flask were put 1.3 g (5.5 mmol) of 4-n-butylbenzyl bromide, 1.4 g (6.6 mmol) of trans-4-(4'-n-propylcyclohexyl)phenol, 0.9 g (6.6 mmol) of potassium carbonate, and 30 mL of acetone. The mixture was degassed while being stirred under reduced pressure. After the degassing, the atmosphere in the flask was replaced with nitrogen. Then, stirring was performed at 70° C. for 6 hours.

Toluene and water were added to the obtained mixture to extract an organic layer, and an aqueous layer was subjected to extraction with toluene. The obtained extract solution and the organic layer were combined, washed with water and a saturated aqueous solution of sodium chloride, and then dried with magnesium sulfate. This mixture was separated by gravity filtration and the filtrate was concentrated and subjected to suction filtration through Celite (produced by Wako Pure Chemical Industries, Ltd., Catalog No. 531-16855), alumina, Florisil (produced by Wako Pure Chemical Industries, Ltd., Catalog No. 540-00135), and silica gel. The obtained filtrate was concentrated to give a light brown solid. This solid was purified by HPLC (the developing solvent was chloroform). The obtained fraction was concentrated to give 1.4 g of a white solid, which was an objective substance, in a yield of 70%.

By a train sublimation method, this solid was purified. In the purification by sublimation, the white solid was heated at 150° C. under a pressure of 2.6 Pa with a flow rate of argon of 10 mL/min. After the purification by sublimation, 0.72 g of a white solid of 1-(4-n-butylbenzyloxy)-4-(trans-4-n-propylcyclohexyl)benzene, which was the objective substance, was obtained as a collection rate of 51%. The synthesis scheme of Step 1 is shown in (E3-1) below.

[Chemical Formula 12]

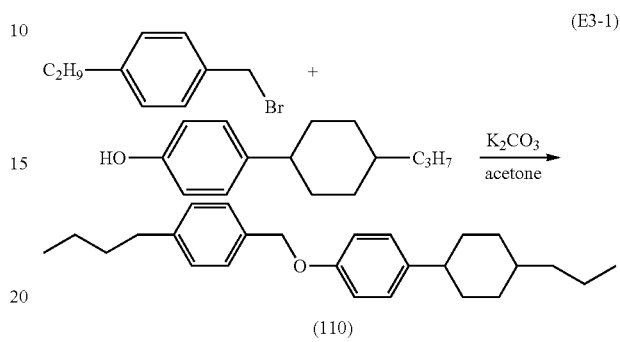

(E3-1)

This compound was identified as 1-(4-n-butylbenzyloxy)-4-(trans-4-n-propylcyclohexyl)benzene (abbreviation: Dal-PCH2OPC-4,3), which was the objective substance, by NMR spectroscopy.

Figure 10A:
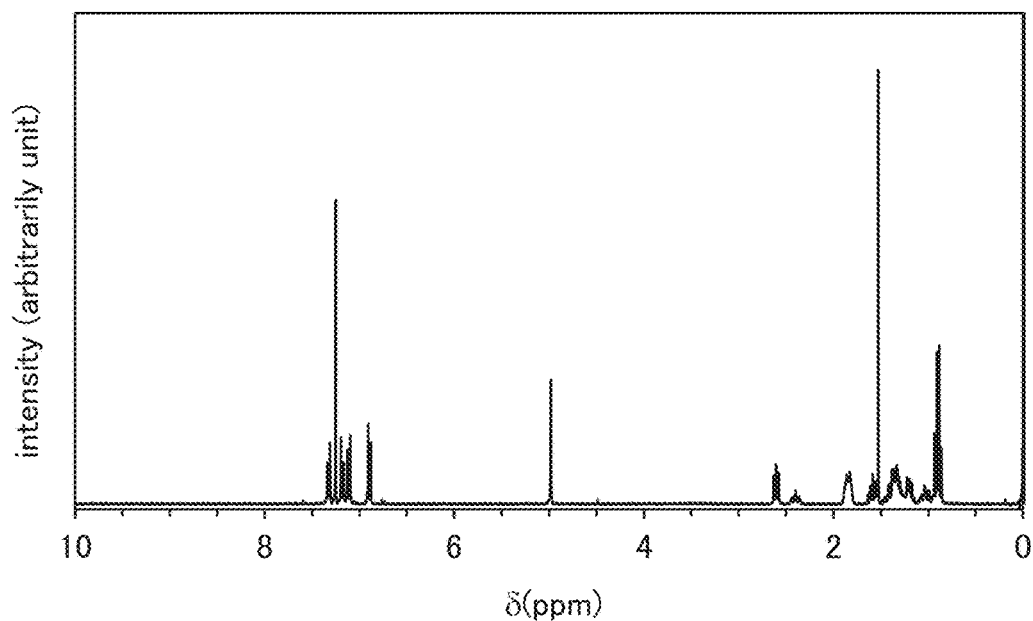
FIGS. 10A and 10B are $^1$H NMR charts of Dal-PCH2OPC-4,3.
Figure 10B:
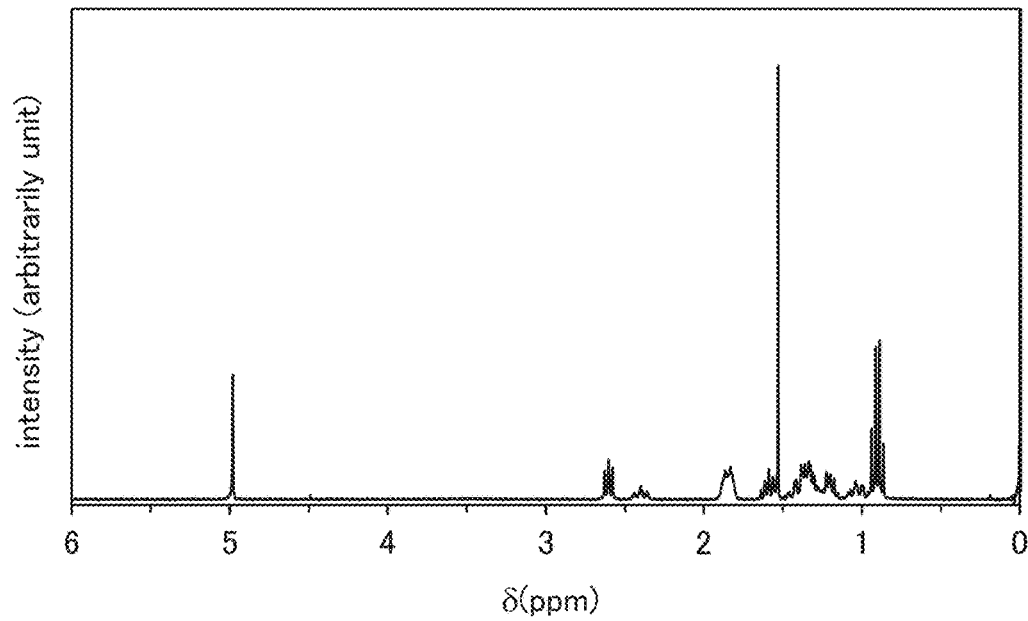
Figure 11:
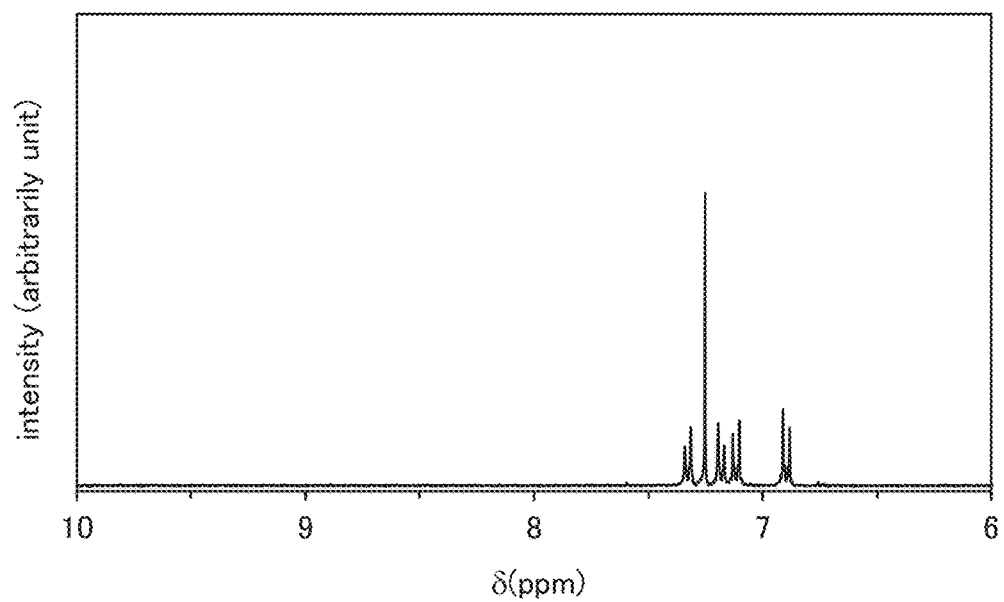
FIG. 11 is a $^1$H NMR chart of Dal-PCH2OPC-4,3.

The $^1$H NMR data of Dal-PCH2OPC-4,3, the obtained substance, is shown below. FIGS. 10A and 10B and FIG. 11 show NMR charts. FIG. 10B is an enlarged chart showing a range of 0 ppm to 6.0 ppm in FIG. 10A. FIG. 11 is an enlarged chart showing a range of 6.0 ppm to 10 ppm in FIG. 10A.

$^1$H NMR (CDC$_3$, 300 MHz): δ (ppm)=0.86-0.94 (m, 6H), 0.99-1.07 (m, 2H), 1.18-1.43 (m, 9H), 1.54-1.61 (m, 2H), 1.81-1.89 (m, 4H), 2.40-2.41 (m, 2H), 2.60 (t, 3H), 4.98 (s, 2H), 6.89 (d, 2H), 7.11 (d, 2H), 7.20 (d, 2H), 7.29 (d, 2H).

Figure 12:
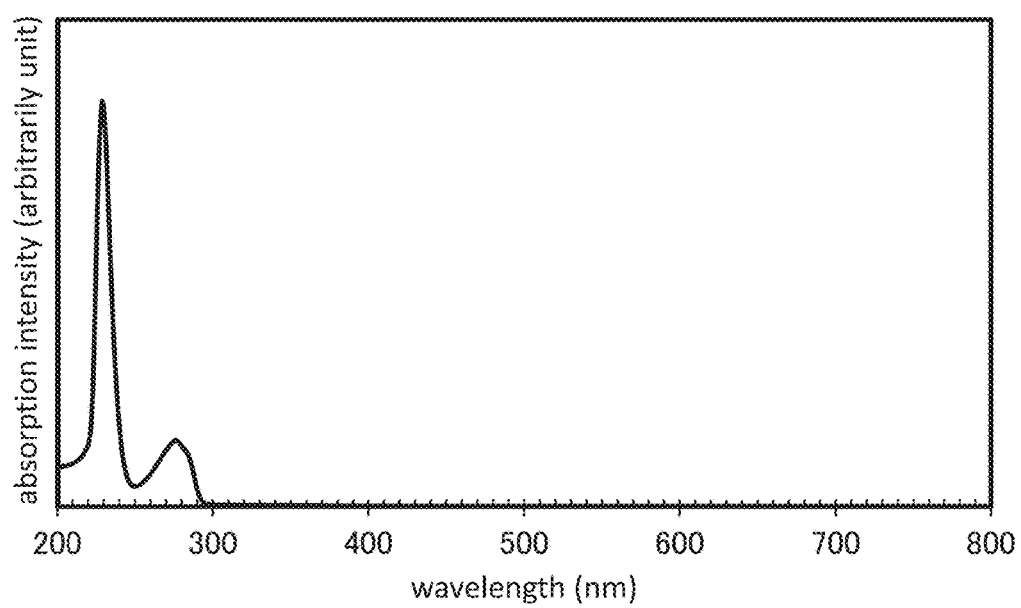
FIG. 12 shows an absorption spectrum of Dal-PCH2OPC-4,3 in a dichloromethane solution of Dal-PCH2OPC-4,3.

FIG. 12 shows an absorption spectrum of Dal-PCH2OPC-4,3 in a dichloromethane solution of Dal-PCH2OPC-4,3.

Example 4

In this example, liquid crystal elements were formed and voltage holding characteristics thereof were examined. The liquid crystal elements were formed by using liquid crystal compositions of Samples 1 to 6 and liquid crystal compositions of Comparative Samples 1 and 2. Dal-PPCH2OP-3 which was synthesized in Example 1 and one embodiment of the present invention, Dal-PCH2OPP-4,3 which was synthesized in Example 2 and one embodiment of the present invention, and Dal-PCH2OPC-4,3 which was synthesized in Example 3 and one embodiment of the present invention were used to form the liquid crystal elements of Samples 1 to 6. None of the organic compounds of embodiments of the present invention was contained in the liquid crystal compositions of Comparative Samples 1 and 2, for comparison.

Components of the liquid crystal compositions used in the liquid crystal elements in this example are listed in Table 1 (Sample 1), Table 2 (Sample 2), Table 3 (Sample 3), Table 4 (Sample 4), Table 5 (Sample 5), and Table 6 (Sample 6). The ratios (the mixture ratios) are all represented in weight ratios.

TABLE 1

| Component | Ratio (wt %) |
| --- | --- |
| MLC-7030 | 94.96 |
| Dal-PPCH2OP-3 | 5.04 |

TABLE 2

| Component | Ratio (wt %) |
| --- | --- |
| E-8 | 95.04 |
| Dal-PPCH2OP-3 | 4.96 |

TABLE 3

| Component | Ratio (wt %) |
| --- | --- |
| MLC-7030 | 95.03 |
| Dal-PCH2OPP-4,3 | 4.97 |

TABLE 4

| Component | Ratio (wt %) |
| --- | --- |
| E-8 | 97.42 |
| Dal-PCH2OPP-4,3 | 2.58 |

TABLE 5

| Component | Ratio (wt %) |
| --- | --- |
| MLC-7030 | 94.87 |
| Dal-PCH2OPC-4,3 | 5.13 |

TABLE 6

| Component | Ratio (wt %) |
| --- | --- |
| E-8 | 95.08 |
| Dal-PCH2OPC-4,3 | 4.92 |

Comparative Sample 1 was a liquid crystal composition in which none of Dal-PPCH2OP-3, Dal-PCH2OPP-4,3, and Dal-PCH2OPC-4,3 were added to a mixed liquid crystal MLC-7030 (produced by Merck Ltd.) used as the base material in each of Samples 1, 3, and 5. Comparative Sample 2 was a liquid crystal composition in which none of Dal-PPCH2OP-3, Dal-PCH2OPP-4,3, and Dal-PCH2OPC-4,3 were added to a mixed liquid crystal E-8 (produced by LCC Corporation) used as the base material in each of Samples 2, 4, and 6. The mixed liquid crystal MLC-7030 and the mixed liquid crystal E-8 each have a positive dielectric constant anisotropy.

The liquid crystal elements including Samples 1 to 6 were each formed in the following manner. Glass substrates each provided with a transparent electrode layer and an alignment film were bonded using a sealant so that the alignment films were positioned between the glass substrates and a space (2 μm) was provided between the alignment films. Then, the liquid crystal compositions formed by mixing the materials in Tables 1 to 6 in the listed ratios were each stirred in an isotropic phase and injected between the substrates by an injection method.

The liquid crystal elements including Comparative Samples 1 and 2 were each formed by injecting the mixed liquid crystal MLC-7030 or the mixed liquid crystal E-8 into a similar cell.

The transparent electrode layer was formed using indium tin oxide containing silicon oxide (ITSO) by a sputtering method. Note that the thickness of the transparent electrode layer was 110 nm. A thermosetting sealant was used as the sealant, which was cured by being subjected to heat treatment at 160° C. for 6 hours under a pressure of 0.3 kgf/cm$^2$.

After that, voltage holding ratios of these samples were measured with the use of the LC material characteristics measurement system model 6254 (manufactured by TOYO Corporation). Measurement conditions were as follows: a selection period was 60 usec, a non-selection period was 16.67 msec or 1000 msec, voltage applied during the selection period was 5 V, and measurement temperature was 30° C. The ratio of the holding voltage after 16.67 msec or 1000 msec to the applied voltage of 5 V was measured as the voltage holding ratio.

Figure 8A:
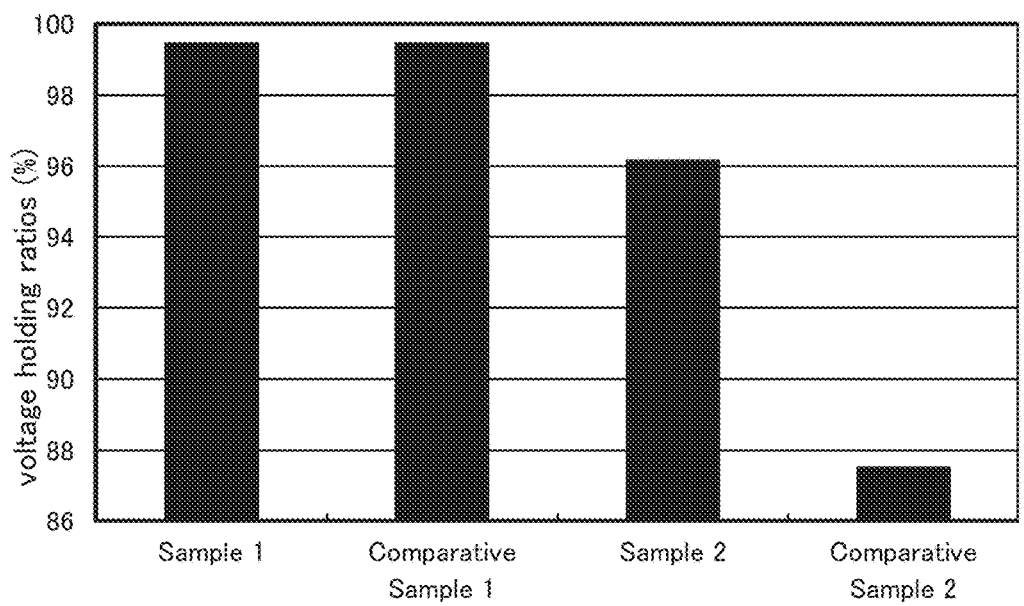
FIGS. 8A and 8B each show the voltage holding ratios of liquid crystal elements formed in Example.
Figure 8B:
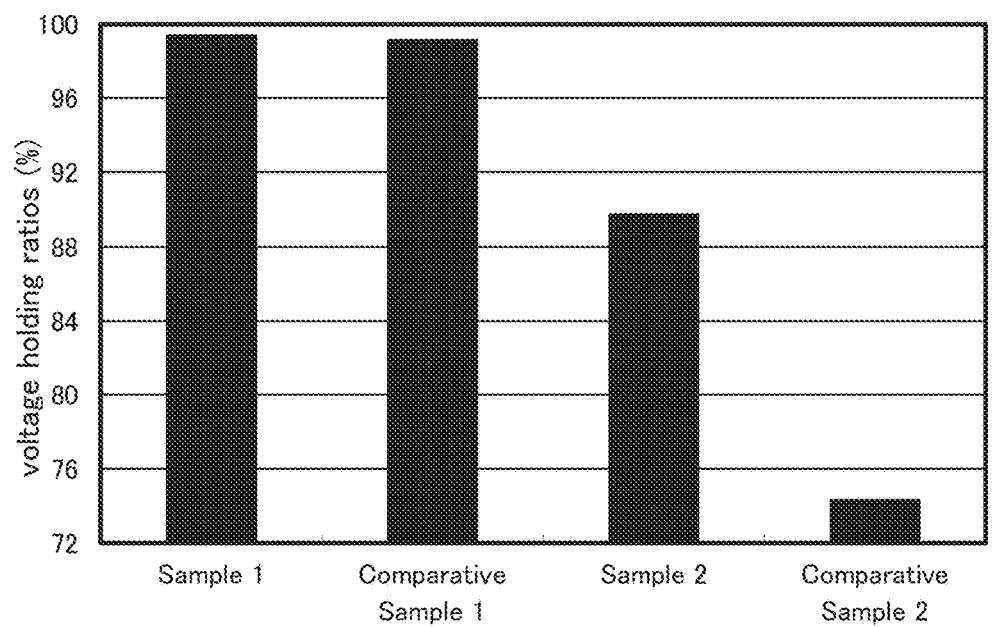

The voltage holding ratios of Samples 1 and 2 and Comparative Samples 1 and 2 are shown in FIGS. 8A and 8B. FIG. 8A shows a measurement result in the case where the non-selection period was 16.67 msec. FIG. 8B shows a measurement result in the case where the non-selection period was 1000 msec.

As shown in FIGS. 8A and 8B, Sample 1 in which Dal-PPCH2OP-3 was added to MLC-7030 (Comparative Sample 1) having a high voltage holding ratio exhibits voltage holding characteristics equivalent to those of Comparative Sample 1. This reveals that addition of Dal-PPCH2OP-3 does not impair the voltage holding characteristics of MLC-7030 and the high voltage holding characteristics can be maintained. Meanwhile, Sample 2 in which Dal-PPCH2OP-3 was added to E-8 (Comparative Sample 2) having a low voltage holding ratio exhibits higher voltage holding characteristics than Comparative Sample 2. This reveals that addition of Dal-PPCH2OP-3 allows formation of a liquid crystal element with a high voltage holding ratio regardless of the base material in the liquid crystal composition.

Figure 9A:
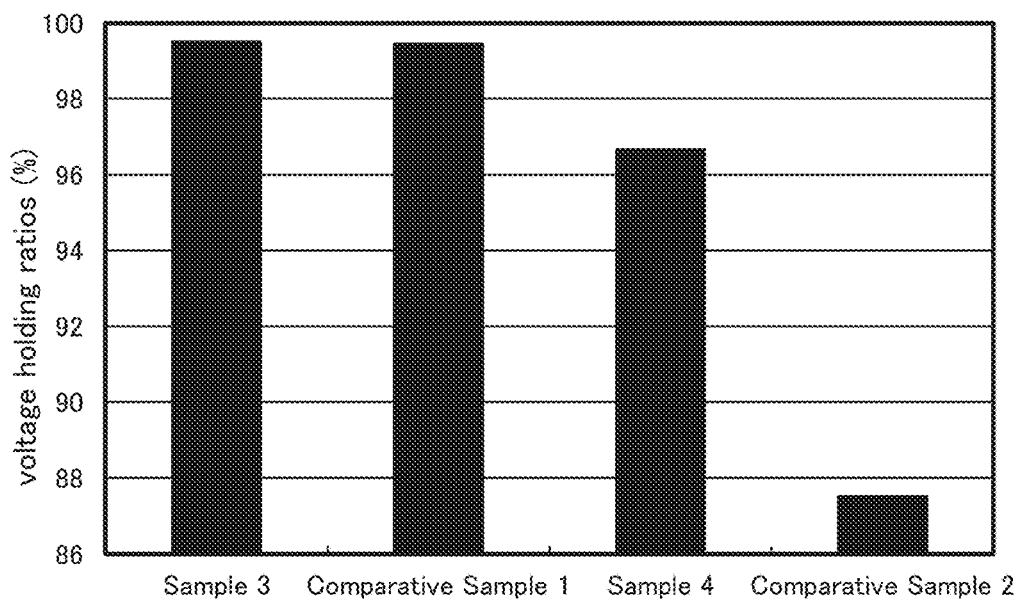
FIGS. 9A and 9B each show the voltage holding ratios of liquid crystal elements formed in Example.
Figure 9B:
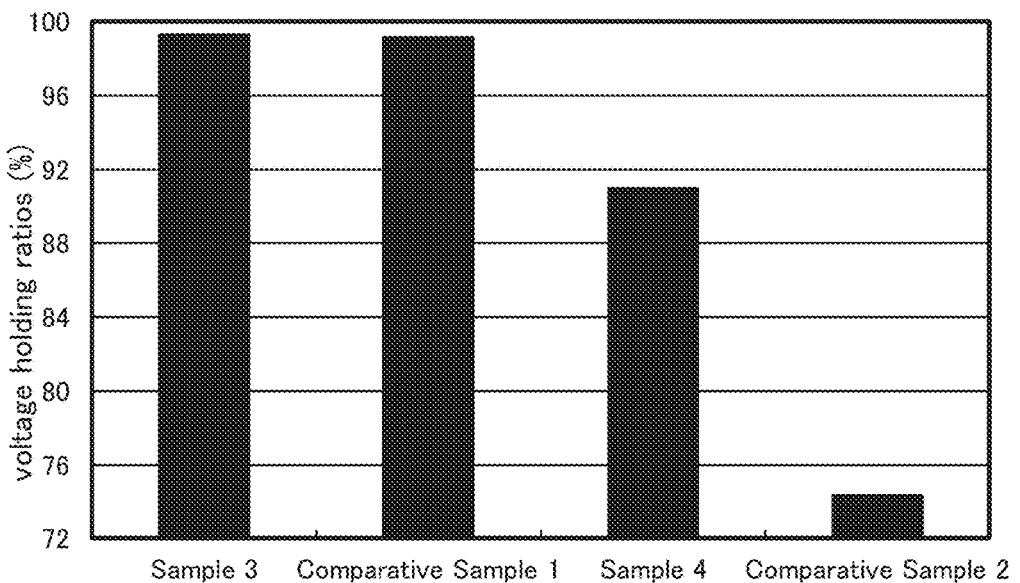

The voltage holding ratios of Samples 3 and 4 and Comparative Samples 1 and 2 are shown in FIGS. 9A and 9B. FIG. 9A shows a measurement result in the case where the non-selection period was 16.67 msec. FIG. 9B shows a measurement result in the case where the non-selection period was 1000 msec.

As shown in FIGS. 9A and 9B, Sample 3 in which Dal-PCH2OPP-4,3 was added to MLC-7030 (Comparative Sample 1) having a high voltage holding ratio exhibits voltage holding characteristics equivalent to those of Comparative Sample 1. This reveals that addition of Dal-PCH2OPP-4,3 does not impair the voltage holding characteristics of MLC-7030 and the high voltage holding characteristics can be maintained. Meanwhile, Sample 4 in which Dal-PCH2OPP-4,3 was added to E-8 (Comparative Sample 2) having a low voltage holding ratio exhibits higher voltage holding characteristics than Comparative Sample 2. This reveals that addition of Dal-PCH2OPP-4,3 allows formation of a liquid crystal element with a high voltage holding ratio regardless of the base material in the liquid crystal composition.

Figure 13A:
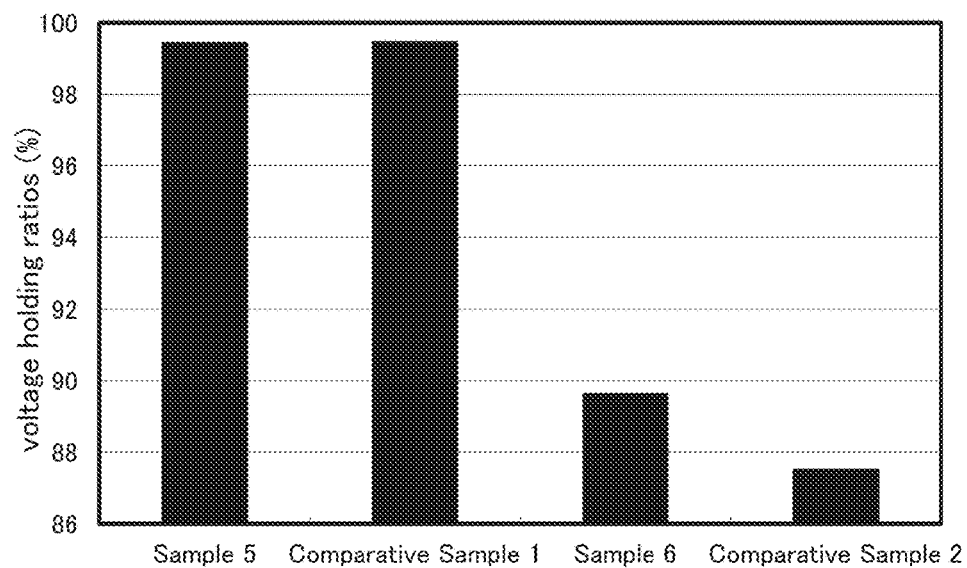
FIGS. 13A and 13B show the voltage holding ratios of liquid crystal elements formed in Example.
Figure 13B:
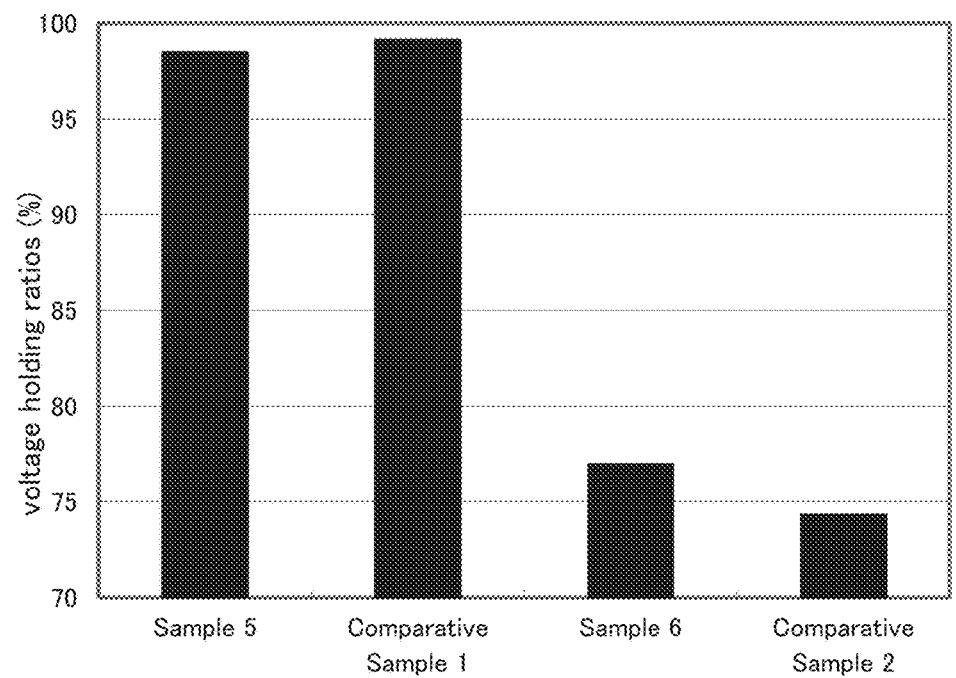

The voltage holding ratios of Samples 5 and 6 and Comparative Samples 1 and 2 are shown in FIGS. 13A and 13B. FIG. 13A shows a measurement result in the case where the non-selection period was 16.67 msec. FIG. 13B shows a measurement result in the case where the non-selection period was 1000 msec.

As shown in FIGS. 13A and 13B, Sample 5 in which Dal-PCH2OPC-4,3 was added to MLC-7030 (Comparative Sample 1) having a high voltage holding ratio exhibits voltage holding characteristics equivalent to those of Comparative Sample 1. This reveals that addition of Dal-PCH2OPC-4,3 does not impair the voltage holding characteristics of MLC-7030 and the high voltage holding characteristics can be maintained. Meanwhile, Sample 6 in which Dal-PCH2OPC-4,3 was added to E-8 (Comparative Sample 2) having a low voltage holding ratio exhibits higher voltage holding characteristics than Comparative Sample 2. This reveals that addition of Dal-PCH2OPC-4,3 allows formation of a liquid crystal element with a high voltage holding ratio regardless of the base material in the liquid crystal composition.

Accordingly, when a liquid crystal composition containing any of Dal-PPCH2OP-3, Dal-PCH2OPP-4,3, and Dal-PCH2OPC-4,3 which are organic compounds of embodiments of the present invention is used in a liquid crystal element, the liquid crystal element can have a high voltage holding ratio. This is because a liquid crystal composition containing any of Dal-PPCH2OP-3, Dal-PCH2OPP-4,3, and Dal-PCH2OPC-4,3 which are organic compounds of embodiments of the present invention has high resistivity.

Samples 1 to 6 in this example have a high voltage holding ratio; thus, when a liquid crystal element including any of the samples is used for a liquid crystal display device, power consumption of the liquid crystal display device can be reduced. In addition, even when a driving method with a lower refresh rate is employed, driving can be performed without loss of display quality.

This application is based on Japanese Patent Application serial no. 2013-157919 filed with Japan Patent Office on Jul. 30, 2013, the entire contents of which are hereby incorporated by reference.

What is claimed is:

1. An organic compound represented by Formula (G1):

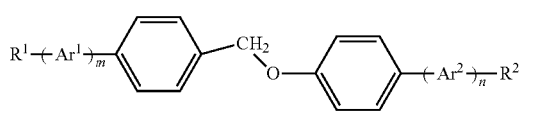

(G1)

wherein $Ar^1$ and $Ar^2$ separately represent a substituted or unsubstituted cycloalkylene group having 3 to 12 carbon atoms, or a substituted or unsubstituted cycloalkenylene group having 3 to 12 carbon atoms,
wherein m represents 1,
wherein n represents 0 or 1 1, and
wherein $R^1$ and $R^2$ separately represent a hydrogen atom or a substituted or unsubstituted alkyl group having 1 to 11 carbon atoms.

2. The organic compound according to claim 1, wherein a substituent of the substituted cycloalkylene group or the substituted cycloalkenylene group of $Ar^1$ or $Ar^2$ is one selected from the group consisting of fluorine (F), bromine (Br), chlorine (Cl), iodine (I), a cyano group (CN), a trifluoromethyl group ($CF_3$), a trifluoromethylsulfonyl group ($SO_2CF_3$), a nitro group ($NO_2$), an isothiocyanate group (NCS), a thiocyanate group (SCN), and a pentafluorosulfanyl group ($SF_5$), and wherein a substituent of the substituted alkyl group of $R^1$ or $R^2$ is one selected from the group consisting of fluorine (F), bromine (Br), chlorine (Cl), iodine (I), a cyano group (CN), a trifluoromethyl group ($CF_3$), a trifluoromethylsulfonyl group ($SO_2CF_3$), a nitro group ($NO_2$), an isothiocyanate group (NCS), a thiocyanate group (SCN), and a pentafluorosulfanyl group ($SF_5$).

3. An organic compound represented by Formula (110):

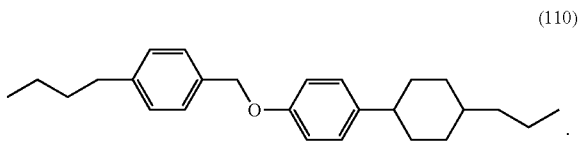

(110)

4. A liquid crystal composition comprising:
a liquid crystal compound; and
an organic compound represented by Formula (G1):

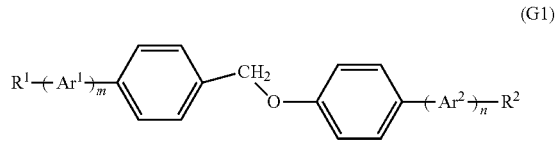

(G1)

wherein $Ar^1$ and $Ar^2$ separately represent a substituted or unsubstituted cycloalkylene group having 3 to 12 carbon atoms, or a substituted or unsubstituted cycloalkenylene group having 3 to 12 carbon atoms,
wherein m represents 1,
wherein n represents 0 or 1, and
wherein $R^1$ and $R^2$ separately represent a hydrogen atom, a substituted or unsubstituted alkyl group having 1 to 11 carbon atoms, or a substituted or unsubstituted alkoxy group having 1 to 11 carbon atoms.

5. The liquid crystal composition according to claim 4, wherein a substituent of the substituted cycloalkylene group or the substituted cycloalkenylene group of $Ar^1$ or $Ar^2$ is one selected from the group consisting of fluorine (F), bromine (Br), chlorine (CO, iodine (I), a cyano group (CN), atrifluoromethyl group ($CF_3$), a trifluoromethylsulfonyl group ($SO_2CF_3$), a nitro group ($NO_2$), an isothiocyanate group (NCS), a thiocyanate group (SCN), or a pentafluorosulfanyl group ($SF_5$), and wherein a substituent of the substituted alkyl group of $R^1$ or $R^2$ is one selected from the group consisting of fluorine (F), bromine (Br), chlorine (Cl), iodine (I), a cyano group (CN), a trifluoromethyl group ($CF_3$), a trifluoromethylsulfonyl group ($SO_2CF_3$), a nitro group ($NO_2$), an isothiocyanate group (NCS), a thiocyanate group (SCN), and a pentafluorosulfanyl group ($SF_5$).

6. A liquid crystal composition comprising:
a liquid crystal compound; and
an organic compound represented by Formula (110):

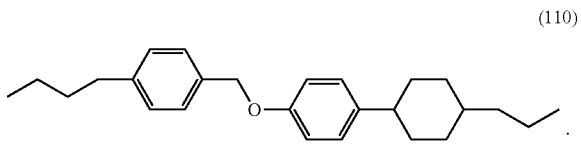

(110)

7. A liquid crystal element comprising the liquid crystal composition according to claim 4.

8. A liquid crystal display device comprising the liquid crystal element according to claim 7.

9. The liquid crystal element according to claim 7, wherein the liquid crystal element has a high voltage holding ratio.

* * * * *

UNITED STATES PATENT AND TRADEMARK OFFICE
CERTIFICATE OF CORRECTION

PATENT NO. : 9,957,213 B2
APPLICATION NO. : 14/330012
DATED : May 1, 2018
INVENTOR(S) : Momoko Kato et al.

It is certified that error appears in the above-identified patent and that said Letters Patent is hereby corrected as shown below:

In the Claims

Column 27, Line 55, Claim 1, "$n$ represents 0 or 1 1," should read --$n$ represents 0 or 1,--

Column 28, Line 44, Claim 5, "chlorine (CO, iodine" should read --chlorine (Cl), iodine--

Column 28, Lines 44 and 45, Claim 5, "atrifluoromethyl" should read --a trifluoromethyl--

Signed and Sealed this
Fourth Day of September, 2018

Andrei Iancu
*Director of the United States Patent and Trademark Office*